United States Patent
Ma et al.

(10) Patent No.: US 12,275,752 B2
(45) Date of Patent: Apr. 15, 2025

(54) CLASS OF PHOSPHINE NITROGEN LIGAND WITH MULTIPLE CHIRAL CENTERS AND ITS SYNTHESIS METHOD AND APPLICATION

(71) Applicant: SHANGHAI INSTITUTE OF ORGANIC CHEMISTRY, CHINESE ACADEMY OF SCIENCES, Shanghai (CN)

(72) Inventors: Shengming Ma, Shanghai (CN); Qi Liu, Shanghai (CN); Haibo Xu, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 705 days.

(21) Appl. No.: 17/618,102

(22) PCT Filed: May 13, 2020

(86) PCT No.: PCT/CN2020/090004
§ 371 (c)(1),
(2) Date: Dec. 10, 2021

(87) PCT Pub. No.: WO2020/248756
PCT Pub. Date: Dec. 17, 2020

(65) Prior Publication Data
US 2022/0332739 A1    Oct. 20, 2022

(30) Foreign Application Priority Data
Jun. 13, 2019 (CN) .......................... 201910513442.9

(51) Int. Cl.
*C07F 9/6509* (2006.01)

(52) U.S. Cl.
CPC .... *C07F 9/650905* (2013.01); *C07B 2200/07* (2013.01)

(58) Field of Classification Search
CPC .................. C07F 9/650905; C07B 2200/07
See application file for complete search history.

(56) References Cited

U.S. PATENT DOCUMENTS 9,994,599 B2 * 6/2018 Aponick .............. B01J 31/2447
10,618,922 B2 * 4/2020 Aponick .............. C07F 9/6506

OTHER PUBLICATIONS

Liu, Nature Communications, 2021, 12:19, 1-10. (Year: 2021).*

* cited by examiner

*Primary Examiner* — D Margaret M Seaman
(74) *Attorney, Agent, or Firm* — Birch, Stewart, Kolasch & Birch, LLP

(57) ABSTRACT

The present invention discloses a phosphine nitrogen ligand with multiple chiral centers and its synthesis method and application. The ligand has the axial chirality of a biaryl skeleton and the central chirality of a chiral amine. The chiral ligand is synthesized from commercially available raw materials through a simple five-step reaction, and the resulting diastereomer can be separated by simple column chromatography or recrystallization. The chiral phosphine nitrogen ligand synthesized by the present invention can catalyze the asymmetric three-component coupling reaction of terminal alkynes, aldehydes and amines, and realize the efficient preparation of chiral propargyl amines with high optical activity.

9 Claims, No Drawings

CLASS OF PHOSPHINE NITROGEN LIGAND WITH MULTIPLE CHIRAL CENTERS AND ITS SYNTHESIS METHOD AND APPLICATION

TECHNICAL FIELD

The present invention belongs to the technical field of chemical synthesis, particularly to a class of phosphine nitrogen ligand with multiple chiral centers and its synthesis method and application.

BACKGROUND OF THE INVENTION

Phosphine nitrogen ligand with axial chirality is an important class of chiral ligands. Since J. M. Brown first published the synthesis of QUINAP in 1993 (*Tetrahedron: Asymmetry* 1993, 4, 743), the ligands have been widely used in various types of asymmetric catalytic reactions (*Tetrahedron* 2001, 57, 3809; *Chem. Soc. Rev.* 2014, 43, 819; *J Org. Chem.* 2014, 79, 5391; *ACS Catal.* 2017, 8, 624). Although similar axial chiral phosphine-nitrogen ligands have been designed and synthesized subsequently, most of them require the resolution and preparation of expensive equivalent chiral palladium complexes, which limits their application. PINAP ligand subsequently reported by E. M. Carreira (*Angew. Chem., Int. Ed.* 2004, 43, 5971) and Stackphim ligand reported by A. Aponick and P. J. Guiry respectively introduce multiple chiral centers (*ACS Catal.* 2017, 7, 2133; *ACS Catal.* 2017, 7, 2334), allowing the corresponding axial chiral phosphine nitrogen ligand to be isolated and purified by column chromatography or recrystallization. However, the axial chiral phosphine nitrogen ligand developed at present is limited in quantity and has great limitations in some asymmetric catalytic reactions showing low reactivity and great substrate limitations. Therefore, it is important to further develop more types of axial chiral phosphine nitrogen ligands with a wider application range and excellent enantioselectivity.

In addition, chiral propargyl amine compounds are an important class of organic chemical structural units. On the one hand, they widely exist in the molecular structures of natural products and drugs; on the other hand, they are important synthetic blocks in organic synthesis and can be transformed into a variety of molecular structures. The asymmetric three-component coupling reaction of terminal alkynes, aldehydes and amines is an efficient and convenient method to synthesize these molecules. However, the previously reported methods have the following limitations: terminal alkynes substrates are limited to substrate with large steric hindrance groups; the reactivity of aromatic aldehydes is low; the reaction time is relatively long. Therefore, it is of great significance to develop an efficient catalytic asymmetric synthesis method of optically active propargyl amine compounds.

SUMMARY OF THE INVENTION

The object of the present invention is to provide a class of phosphine nitrogen ligand with multiple chiral centers and its synthesis method and application.

The present invention provides a phosphine nitrogen ligand with multiple chiral centers, which has the following structure:

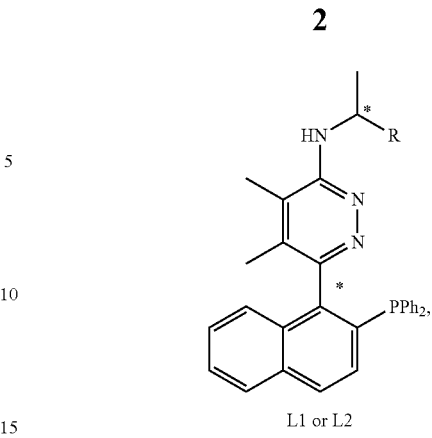

L1 or L2 wherein, *represents the chiral center

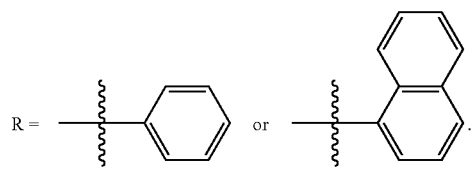

Furthermore, the phosphine nitrogen ligand with multiple chiral centers includes the following structures:

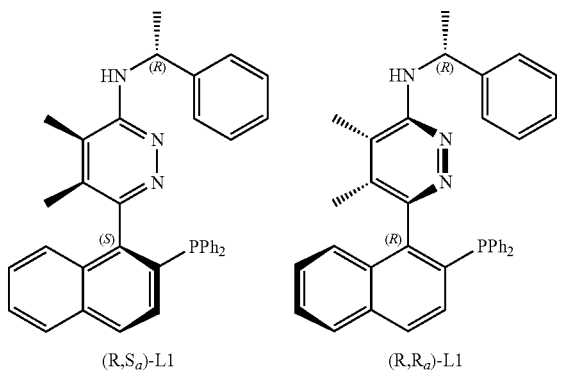

(R,S$_a$)-L1    (R,R$_a$)-L1

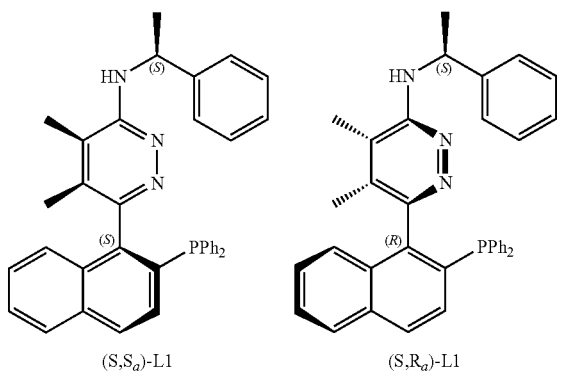

(S,S$_a$)-L1    (S,R$_a$)-L1

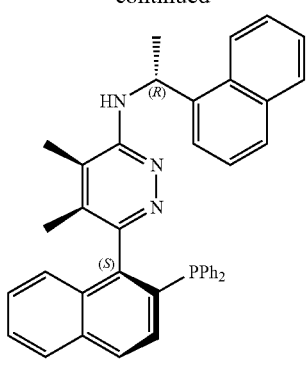
(R,S_a)-L2
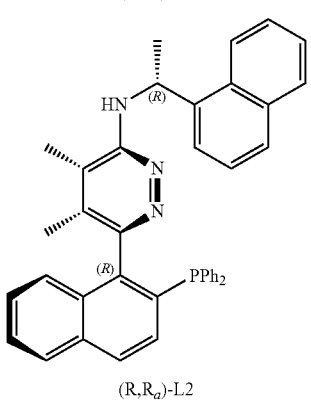
(R,R_a)-L2
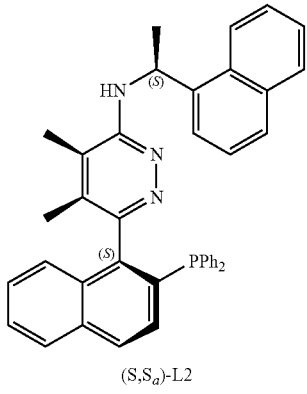
(S,S_a)-L2
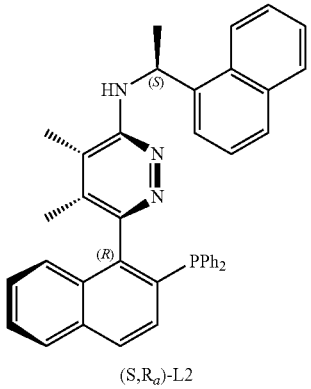
(S,R_a)-L2
The present invention also provides a synthesis method for a class of phosphine nitrogen ligand with multiple chiral centers and the reaction equation is as follows:
Equation (A)
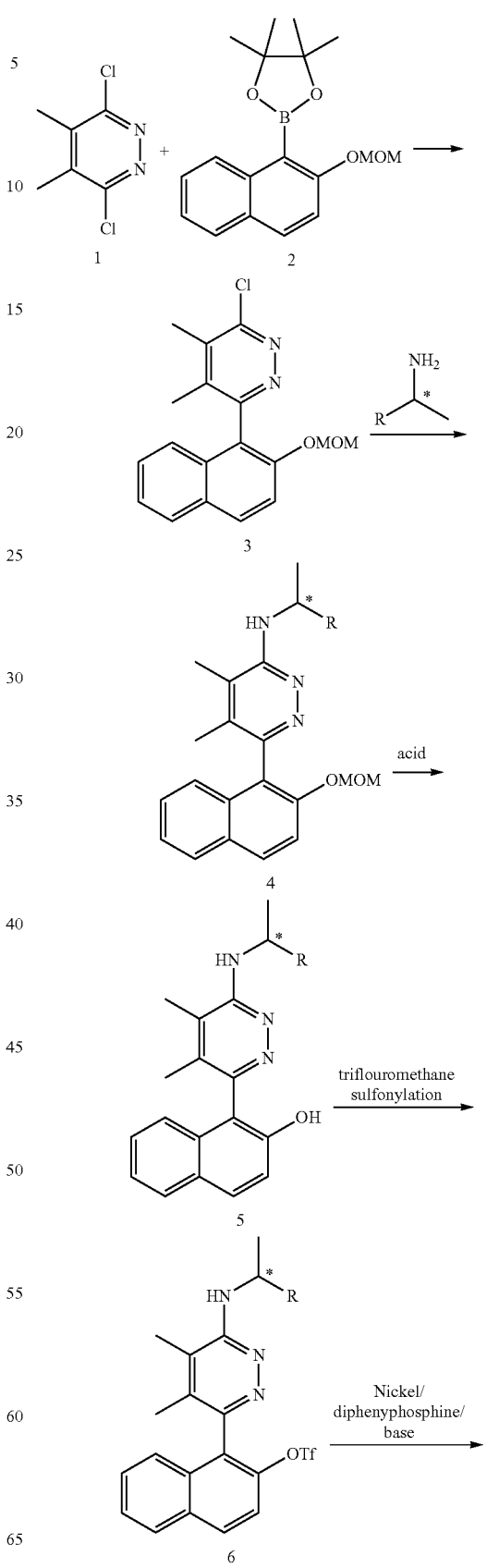

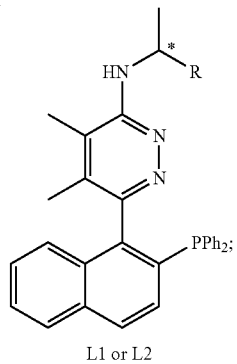

L1 or L2

Wherein,

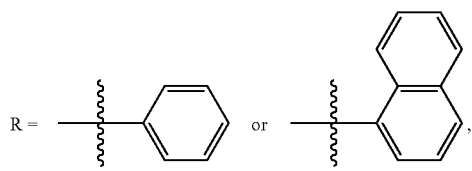

*represents the chiral center.

The steps include:
(1) in the solvent, 3,6-dichloro-4,5-dimethylpyridazine and borate ester compounds are taken as raw materials to react to obtain biaryl compounds, in the presence of base, with palladium salt and phosphine ligand as catalytic system or directly using palladium and phosphine complexes;
(2) in the solvent, the biaryl compounds of step (1) and chiral amine are taken as raw materials, in the presence of base, with palladium salt and phosphine ligand as catalytic system or directly using palladium and phosphine complexes to obtain the amination product through coupling reaction;
(3) in the solvent, the amination product obtained in step (2) reacts with the acid to obtain the phenolic product;
(4) in an organic solvent, in the presence of an acid binding agent, the phenolic products obtained in step (3), trifluoromethanesulfonation reagent reacts with 4-dimethylaminopyridine to obtain the trifluoromethanesulfonation products;
(5) in an organic solvent, the trifluoromethanesulfonation product obtained in step (4), diphenylphosphine and nickel react with an organic base to obtain the phosphine nitrogen ligand with multiple chiral centers.

In step (1), the molar ratio of the said 3,6-dichloro-4,5-dimethylpyridazine:borate ester compound:base:palladium-salt:phosphine ligand is 1:(1~2):(1~2):(0.01~0.2):(0.01~0.4); preferably, the molar ratio of the said 3,6-dichloro-4,5-dimethylpyridazine:borate ester compound:base:palladiumsalt:phosphine ligand is 1:1.4:2:0.05:0.2.

Or the molar ratio of the said 3,6-dichloro-4,5-dimethylpyridazine:borate ester compound:base:palladium and phosphine complex is 1:(1~2):(1~2):(0.01~0.2); preferably, the molar ratio of the said 3,6-dichloro-4,5-dimethylpyridazine:borate ester compound:base:palladium and phosphine complex is 1:1.4:2:0.05.

In step (1), the said base is one or more of sodium bicarbonate, sodium carbonate, sodium hydroxide, potassium bicarbonate, potassium carbonate, potassium hydroxide, potassium phosphate, cesium fluoride or cesium carbonate, etc; preferably, is sodium carbonate.

In step (1), the said palladium salts are one or more of palladium acetate, palladium chloride, palladium dibenzylidenyl acetone, cinnamyl palladium chloride, allyl palladium chloride, palladium trifluoroacetate, palladium diacetyl acetone, palladium diacetonitrile dichloride, or palladium dibenzonitrile dichloride, etc; preferably, is palladium acetate.

In step (1), the said phosphine ligand is one or more of triphenylphosphine, tris (2-furanyl) phosphine, tris (4-methoxyphenyl) phosphine, tris (2,4,6-trimethoxyphenyl) phosphine, 1,1'-binaphthalene-2,2'-bisdiphenylphosphine, tricyclohexylphosphine, tri-n-butylphosphine, tri-tert-butylphosphine, etc; preferably, is triphenylphosphine.

In step (1), the said palladium and phosphine complex is one or more of tetratriphenylphosphine palladium, ditriphenylphosphine palladium dichloride, ditricyclohexylphosphine palladium or ditritert-butylphosphine palladium, etc; preferably, is tetratriphenylphosphine palladium.

In step (1), the said solvent is one or more of water, benzene, toluene, p-xylene, o-xylene, m-xylene, mesitylene, 1,4-dioxane, tetrahydrofuran, ethylene glycol dimethyl ether, N,N-dimethylformamide or dimethyl sulfoxide, etc, preferably, is a mixture of ethylene glycol dimethyl ether and water.

In step (1), the said reaction temperature is 20-200° C.; preferably, is 120° C.

In step (1), the said reaction time is 1-40 hours; preferably, is 24 hours.

In step (2), the molar ratio of the said biaryl compound:chiral amine:base palladium salt:phosphine ligand is 1:(1~2):(1~2):(0.01~0.2):(0.01~0.2); preferably, the molar ratio of the said biaryl compound:chiral amine:base:palladium salt phosphine ligand is 1:1.3:1.4:0.05:0.075.

Or the molar ratio of the said biaryl compound:chiral amine:base:palladium and phosphine complex is 1:(1~2):(1~2):(0.01~0.2); preferably, the molar ratio of the said biaryl compounds:chiral amine:base:palladium and phosphine complexes is 1:1.3:1:4:0.05.

In step (2), the base is one or more of sodium bicarbonate, sodium carbonate, sodium hydroxide, potassium bicarbonate, potassium carbonate, potassium hydroxide, potassium phosphate or cesium carbonate, etc; preferably, is cesium carbonate.

In step (2), the said palladium salts are one or more of palladium acetate, palladium chloride, palladium dibenzylidenyl acetone, cinnamyl palladium chloride, allyl palladium chloride, palladium trifluoroacetate, palladium diacetyl acetone, palladium diacetonitrile dichloride, or palladium dibenzonitrile dichloride, etc; preferably, is palladium acetate.

In step (2), the said phosphine ligand is one or more of triphenylphosphine, tris (2-furanyl) phosphine, tris (4-methoxyphenyl) phosphine, tris (2,4,6-trimethoxyphenyl) phosphine, 1,1'-binaphthalene-2,2'-bisdiphenylphosphine, tricyclohexylphosphine, tri-n-butylphosphine or tri-tert-butylphosphine, etc;. preferably, is 1,1'-binaphthalene-2,2'-bisdiphenylphosphonate.

In step (2), the said palladium and phosphine complex is one or more of tetratriphenylphosphine palladium, ditriphenylphosphine palladium dichloride, ditricyclohexylphosphine palladium or ditritert-butylphosphine palladium, etc; preferably, is tetratriphenylphosphine palladium.

In step (2), the said solvent is one or more of benzene, toluene, p-xylene, o-xylene, m-xylene, mesitylene, tetrahydrofuran, 1,4-dioxane, ethylene glycol dimethyl ether, N,N-dimethylformamide or dimethyl sulfoxide, etc; preferably, is toluene.

In step (2), the said reaction temperature is 20-200° C.; preferably, is 120° C.

In step (2), the said reaction time is 1-20 hours; preferably, is 9 hours.

In step (3), the molar ratio of the said amination product:acid is 1:(1~100); preferably, the molar ratio of the said amination product:acid is 1:30.

In step (3), the said solvent is one or more of methanol, ethanol, isopropanol, water, 1,4-dioxane, tetrahydrofuran, ethylene glycol dimethyl ether, N,N-dimethylformamide or dimethyl sulfoxide, etc; preferably, is a mixture of methanol and water.

In step (3), the said acid is one or more of hydrochloric acid, hydrobromic acid, hydroiodic acid, acetic acid, sulfuric acid, phosphoric acid, trifluoroacetic acid or p-toluenesulfonic acid, etc; preferably, is hydrochloric acid.

In step (3), the said reaction temperature is −20-100° C.; preferably, is 25° C.

In step (3), the said reaction time is 12-36 hours; preferably, is 24 hours.

In step (4), the molar ratio of the said phenolic products trifluoromethosulfonation reagent:acid binding agent:4-dimethylaminopyridine is 1:(1~2):(1~2):(0.01~0.2); preferably, the molar ratio of the said phenolic products trifluoromethosulfonylation reagent:acid binding agent:4-dimethylaminopyridine is 1:1:1:0.1.

In step (4), the said organic solvent is one or more of dichloromethane, 1,2-dichloroethane, N,N-dimethylformamide, tetrahydrofuran, ethylene glycol dimethyl ether or dimethyl sulfoxide, etc; preferably, is dichloromethane.

In step (4), the said acid binding agent is an organic base, selected from 1,4-diazacycle [2.2.2]octane, N,N-diisopropyl ethylamine, triethylamine or pyridine, etc; preferably, is triethylamine.

In step (4), the said trifluoromethanesulfonation reagent is one or more of trifluoromethanesulfonyl anhydride, N-phenylbis (trifluoromethanesulfonyl) imide or trifluoromethanesulfonyl chloride, etc; preferably, is N-phenylbis (trifluoromethanesulfonyl) imide.

In step (4), the said reaction temperature is −20-100° C.; preferably, is 25° C.

In step (4), the said reaction time is 0.5-50 hours; preferably, is 24 hours.

In step (5), the molar ratio of the said trifluoromethosulfonation product:diphenyl phosphine:nickel:the organic base is 1:(1~4):(0.05~0.2):(1~5); preferably, the molar ratio of the said trifluoromethosulfonation product:diphenyl phosphine:nickel organic base is 1:2:0.1:4.

In step (5), the said organic solvent is one or more of N,N-dimethylformamide, N-methylpyrrolidone or dimethyl sulfoxide, etc; preferably, N,N-dimethylformamide.

In step (5), the nickel is one or more of 1,2-bis(diphenylphosphine) ethane nickel chloride, 1,2-bis(diphenylphosphine) propane nickel chloride or 1,2-bis (diphenylphosphine) butane nickel chloride or ditriphenylphosphine nickel chloride, etc; preferably, is 1,2-bis(diphenylphosphine) ethane nickel chloride.

In step (5), the said organic base is one or more of 1,4-diazacycle [2.2.2]octane, N,N-diisopropyl ethylamine, triethylamine or pyridine, etc; preferably, is 1,4-diazacycle [2.2.2]octane.

In step (5), the said reaction temperature is 90-140° C.; preferably, is 120° C.

In step (5), the said reaction time is 6-20 hours; preferably, is 12 hours.

In one embodiment, the steps of the synthesis method of the said phosphine-nitrogen ligand with multiple chiral centers are as follows:

(1) In a mixed solvent of organic solvent and water, at the reflux temperature of 120° C., 3,6-dichloro-4,5-dimethylpyridazine 1, borate compound 2 and an inorganic base react to form the biaryl compound 3 with palladium salt and phosphine ligand as catalytic system or directly using palladium and phosphine complex, and the reaction time is 1-40 hours.

(2) In organic solvent and at the reflux temperature of 120° C., with a base as an additive, palladium salt and phosphine ligand as catalytic system or directly using palladium and phosphine complex, the biaryl compound 3 and chiral amine are coupled to produce the aminated product 4, and the reaction time is 1-20 hours.

(3) In the mixed solvent of alcohol and water at room temperature, aminated product 4 and acid react to obtain phenolic product 5 for 12-36 hours.

(4) In organic solvent, at room temperature, with an organic base as the acid binding agent, the phenolic product 5, trifluoromethosulfonation reagent and 4-dimethylaminopyridine react to obtain the trifluoromethosulfonation product 6 for 0.5-50 hours.

(5) In organic solvent, at 90-140° C., the trifluoromethosulfonation product 6, diphenyl phosphine, nickel and organic base react to obtain ligand L1 or L2 for 6-20 hours.

The specific equation is shown in equation (A') below:

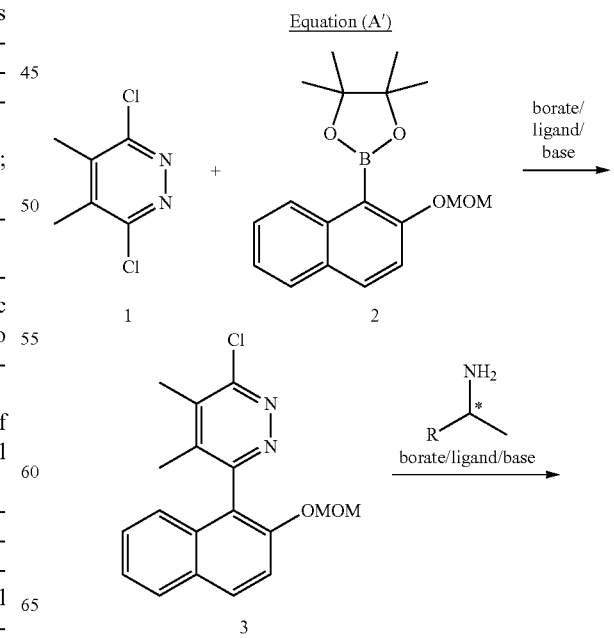

Equation (A')

-continued

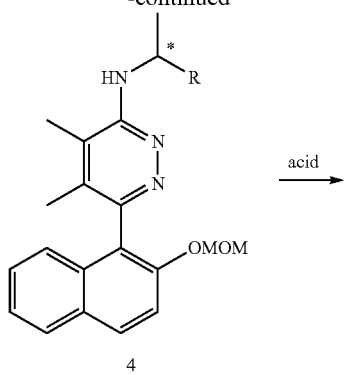

4

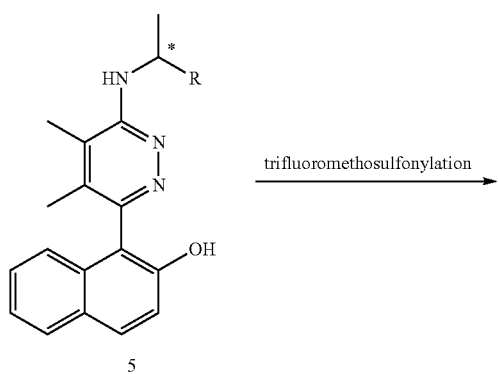

5

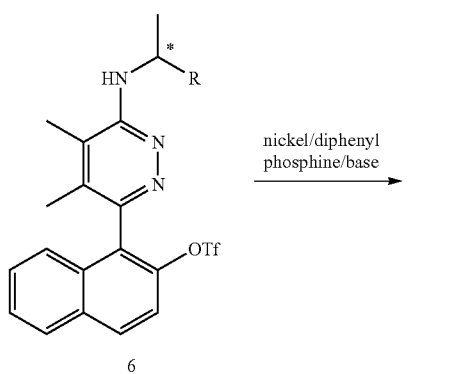

6

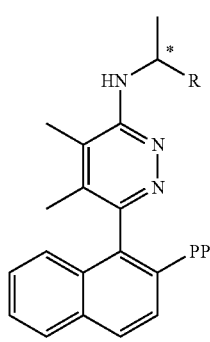

L1 or L2 wherein,

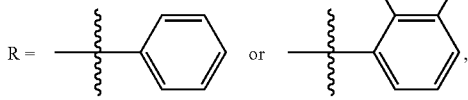

*represents the chiral center.

Wherein, the reaction of steps (1), (2), (4) or (5) is preferably carried out in an inert gas atmosphere. The reaction of step (3) is preferably carried out in an air atmosphere.

Wherein, the reaction product prepared in steps (1), (2), (3), (4) or (5) can be purified by organic solvent extraction, drying or concentration, column chromatography or recrystallization.

The phosphine nitrogen ligand with multiple chiral centers synthesized in the present invention has the axial chirality of a biaryl skeleton and the central chirality of a chiral amine. The diaryl skeleton is composed of pyridazine heterocyclic and naphthalene rings. The introduction of pyridazine heterocyclic is the innovation point of the present invention, and its unique structure and electrical characteristic make the whole ligand have unique catalytic reaction activity. On the other hand, the structure of chiral amines simplifies the preparation and separation of chiral ligands, and the stereochemical control of the ligand in the reaction can be optimized by introducing different structures of chiral amines.

The present invention also proposes a phosphine nitrogen ligand intermediate with multiple chiral centers, which has chemical structures as shown in formulas 3, 4, 5 and 6:

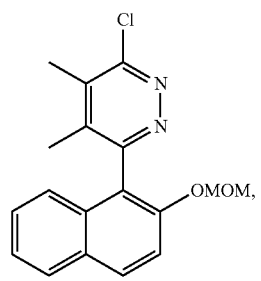

3

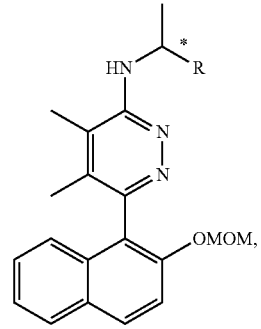

4

-continued

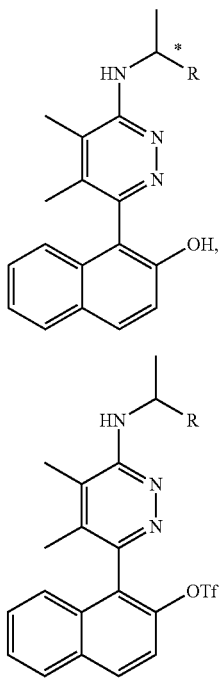

Wherein,

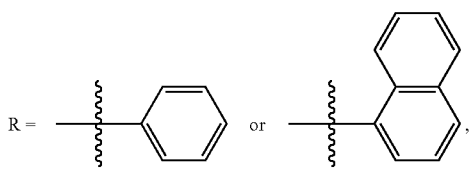

*represents the chiral center.

The chiral phosphine nitrogen ligand synthesized by the present invention can catalyze asymmetric three-component coupling reactions of terminal alkynes, aldehydes and amines, especially for terminal alkynes substrates with small steric hindrance groups, thus achieving efficient and stereoselective preparation of chiral propargyl amine compounds.

The beneficial effect of the invention is that the invention provides a new ligand, which is synthesized from commercially available raw materials through a simple five-step reaction and can be purified only by simple column chromatography separation or recrystallization. The unique chemical structure of the ligand makes it have high catalytic activity and stereochemical control ability, showing excellent properties in asymmetric catalytic reactions. The above characteristics can be illustrated by the following examples.

PREFERRED EMBODIMENTS OF THE INVENTION

The following examples are given for further illustrating the specific solutions of the present invention. The protection of the invention is not limited to the following embodiments. Without departing from the spirit and scope of the idea of the invention, all changes and advantages that can be thought of by a person skilled in the field are included in the invention and are protected by the attached claims. The process, conditions, reagents and experimental methods of the implementation of the invention are all general knowledge and common knowledge in the field except for the contents specially mentioned below, and the present invention has no special limitation. The following embodiments are helpful in understanding the invention but do not limit the scope of protection of the invention.

Note: in the equation of the following embodiments: "equiv" refers to equivalent; "mol" refers to mole; "Ar" refers to argon; "reflux" refers to reflux; "DMAP" refers to 4-dimethylaminopyridine; "DABCO" refers to 1,4-diazacycle [2.2.2]octane; "MS" refers to molecular sieve; "DME" refers to ethylene glycol dimethyl ether; "Toluene" refers to toluene; "DCM" refers to dichloromethane; "THF" refers to tetrahydrofuran; "DMF" refers to N,N-dimethylformamide; "rac-BINAP" refers to rac 1,1'-binaphthalene 2,2'-bisdiphenyl phosphine; "r.t" refers to room temperature; "ee" refers to enantiomeric excess; "d.r." refers to diastereomer ratio.

Example 1

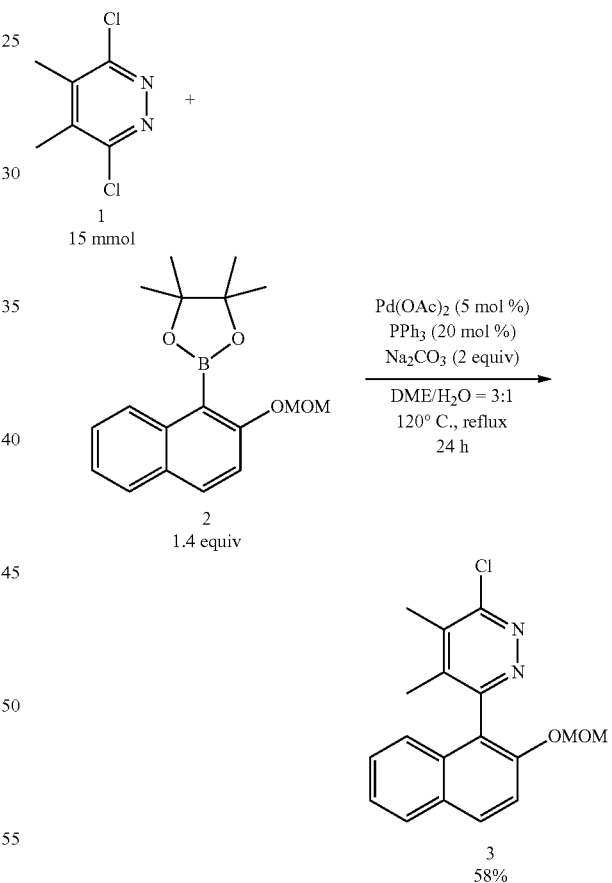

1 (2.7111 g, 15 mmol), 2 (6.6024 g, 21 mmol), Pd(OAc)$_2$ (170.5 mg, 0.75 mmol), PPh$_3$ (787.5 mg, 3 mmol) and Na$_2$CO$_3$ (3.2155 g, 30 mmol) were added to a reaction flask with a reflux condenser. The Ar was replaced from the reaction bottle three times and 44 mL of mixed solvent (ethylene glycol dimethyl ether:water=3:1) was added. The device was stirred in an oil bath preheated to 120° C. and reflux for 24 h until the completion of reaction was confirmed by TLC detection. The device was removed from the oil bath, cooled naturally to room temperature, added 18 mL water and 3×40 mL dichloromethane to extract. The organic phases were combined, dried by anhydrous sodium sulfate, filtered and concentrated and subjected to column chromatography (eluent: petroleum ether/ethyl acetate=10:1 (550 mL) to 5:1 (1560 mL) to 4:1 (250 mL)) to obtain white solid product 3 (2.8810 g, 58%):melting point was 131.9-132.6° C. (ethyl acetate/petroleum ether); $^1$H NMR (400 MHz, CDCl$_3$) δ 7.96 (d, J=9.2 Hz, 1H, ArH), 7.86 (d, J=9.2 Hz, 1H, ArH), 7.53 (d, J=8.8 Hz, 1H, ArH), 7.42-7.32 (m, 2H, ArH), 7.11 (d, J=7.6 Hz, 1H, ArH), 5.17 (d, J=6.8 Hz, 1H, one proton from OCH$_2$O), 5.15 (d, J=6.8 Hz, 1H, one proton from OCH$_2$O), 3.37 (s, 3H, OCH$_3$), 2.50 (s, 3H, CH$_3$), 2.06 (s, 3H, CH$_3$); $^{13}$C NMR (400 MHz, CDCl$_3$) δ 158.7, 157.0, 152.2, 139.9, 135.9, 132.8, 130.9, 129.5, 128.0, 127.1, 124.3, 124.1, 120.6, 116.0, 94.9, 56.1, 15.84, 15.80; MS (ESI) m/z 329 ([M+H]$^+$); IR (neat): v=2947, 2904, 1619, 1592, 1541, 1527, 1506, 1468, 1451, 1435, 1410, 1380, 1338, 1310, 1263, 1245, 1229, 1215, 1195, 1172, 1151, 1104, 1088, 1078, 1030, 1010; the Anal. Calcd. for C$_{18}$H$_{17}$ClN$_2$O$_2$ were C 65.75, H 5.21, N 8.52; found: C 65.63, H 5.08, N 8.27.

Example 2

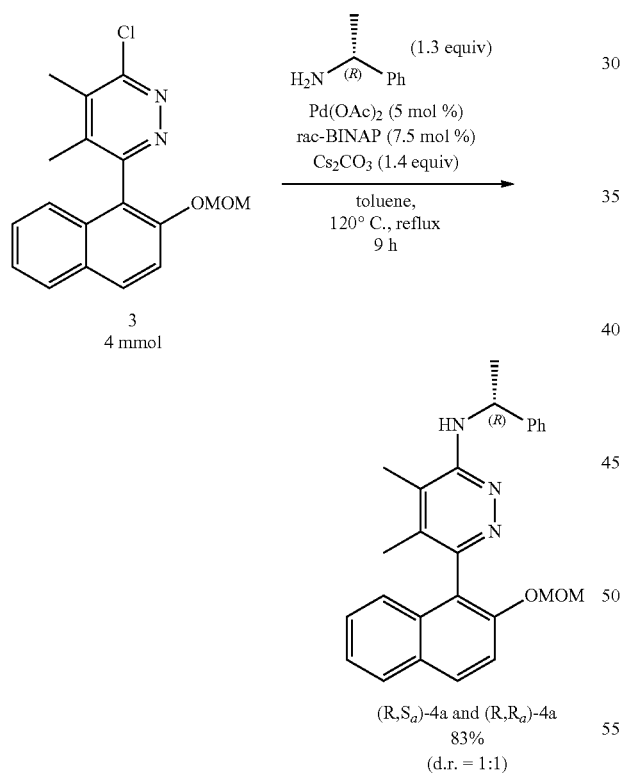

3
4 mmol (R,S$_a$)-4a and (R,R$_a$)-4a
83%
(d.r. = 1:1)

Pd(OAc)$_2$ (46.0 mg, 0.2 mmol), racemate 1,1'-binaphthaline-2,2'-bisdiphenylphosphonate (191.3 mg, 0.3 mmol) and toluene (4 mL) were successively added to a dry reaction flask with a reflux condenser under inert gas protection. After stirring at room temperature for 30 minutes, 3 (1.3188 g, 4 mmol) (R)-1-phenyl-1-ethylamine (0.68 mL, d=0.940 g/mL, 0.6392 g, 5.2 mmol)/toluene (4 mL) and Cs$_2$CO$_3$ (1.8293 g, 5.6 mmol) were added. The mixture was stirred in an oil bath preheated to 120° C. and refluxed for 9 h until the completion of reaction was confirmed by TLC detection. The device was removed from the oil bath, cooled naturally to room temperature, filtered by a short alkaline aluminum oxide column (200-300 mesh) and rinsed with 80 mL ethyl acetate. The filtrate was concentrated and subjected to column chromatography (eluent: petroleum ether/ethyl acetate=4:1 (750 mL) to 3:1 (1200 mL) to 2:1 (750 mL)) to obtain a mixture of yellow solid foam (R,S$_a$)-4a and (R,R$_a$)-4a (1.3726 g, 83%, d.r.=1:1) (d.r. of the product values are determined by nuclear magnetic analysis) whose melting point was 77.7-78.7° C. (as crystals cannot be obtained by recrystallization, melting point was obtained by direct measurement of solids obtained by spin-drying); $^1$H NMR (400 MHz, CDCl$_3$) δ [7.86 (d, J=9.2 Hz, 0.50H), 7.85 (d, J=9.2 Hz, 0.50H), 1H, ArH], 7.81-7.77 (m, 1H, ArH), 7.54-7.42 (m, 3H, ArH), 7.38-7.17 (m, 6H, ArH), 5.72-5.61 (m, 1H, NCH), [5.16 (d, J=6.8 Hz, 0.47H), 5.08 (d, J=6.8 Hz, 0.50H), 1H, OCH$_2$O], [5.08 (d, J=6.8 Hz, 0.50H), 5.00 (d, J=6.4 Hz, 0.47H), 1H, OCH$_2$O], [4.57 (d, J=6.0 Hz, 0.49H), 4.52 (d, J=6.0 Hz, 0.47H), 1H, NH], [3.36 (s, 1.39H), 3.22 (s, 1.46H), 3H, OCH$_3$], 2.06 (s, 3H, CH$_3$), 1.89 (s, 3H, CH$_3$), [1.64 (d, J=6.4 Hz, 1.50H), 1.63 (d, J=6.4 Hz, 1.50H), 3H, CH$_3$]; MS (ESI) m/z 414 ([M+H]$^+$); IR (neat): v=3297, 2966, 2898, 2824, 1622, 1592, 1579, 1556, 1509, 1469, 1446, 1396, 1372, 1355, 1303, 1263, 1241, 1196, 1145, 1074, 1031, 1010; HRMS calcd for C$_{26}$H$_{28}$N$_3$O$_2$ ([M+H]$^+$): 414.2182; found: 414.2162.

Example 3

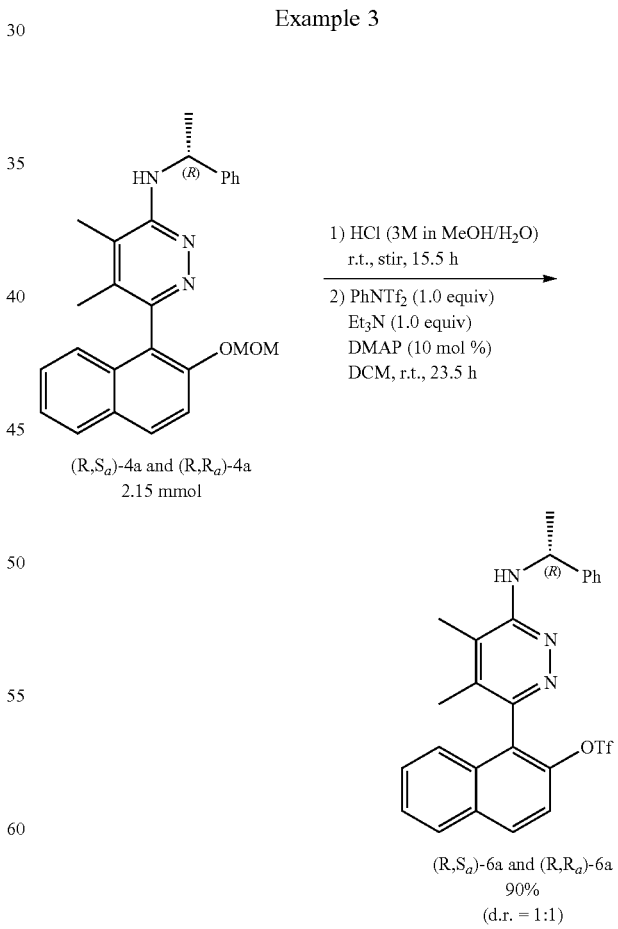

(R,S$_a$)-4a and (R,R$_a$)-4a
2.15 mmol (R,S$_a$)-6a and (R,R$_a$)-6a
90%
(d.r. = 1:1)

The mixture of (R,S$_a$)-4a and (R,R$_a$)-4 (d.r.=1:1, 887.5 mg, 2.15 mmol) and 42.9 mL HCl (3 M mixed solution of MeOH/H₂O) were added to the reaction flask. The mixture was stirred at room temperature for 15.5 h until the completion of the reaction was confirmed by TLC detection. The mixture was neutralized to neutral by concentrated ammonia, diluted with 20 mL water and extracted with 3×40 mL dichloromethane. The organic phases were combined to be dried by anhydrous sodium sulfate, filtered and concentrated to obtain yellow solid foam which could be directly used for the next step without purification.

The crude product obtained in the previous step and 4-dimethylaminopyridine (26.7 mg, 0.215 mmol) were added to the reaction flask. The Ar was replaced from the reaction bottle three times, then 21.5 mL DCM, Et₃N (0.30 mL, d=0.728 g/mL, 0.2184 g, 2.15 mmol) and N-phenylbis(trifluoromethanesulfonyl) imide (784.3 mg, 2.15 mmol) were successively added. The mixture was stirred at room temperature for 23.5 hours until the completion of reaction was confirmed by TLC detection. The mixture was directly concentrated and subjected to column chromatography (eluent: petroleum ether/ethyl acetate=4:1 (750 mL) to 3:1 (1000 mL)) to obtain a mixture of yellow solid foam (R,S$_a$)-6a and (R,R$_a$)-6a (0.9663 g, 90%, d.r.=1:1) (d.r. of the product values determined by nuclear magnetic analysis): melting point was 75.8-76.8° C. (as crystals cannot be obtained by recrystallization, melting point was obtained by direct measurement of solids obtained by spin-drying); ¹H NMR (400 MHz, CDCl₃) δ 7.99 (d, J=8.8 Hz, 1H, ArH), 7.93 (d, J=7.2 Hz, 1H, ArH), 7.59-7.23 (m, 9H, ArH), 5.70 (m, 1H, NCH), [4.54 (s, 0.46H), 4.52 (s, 0.45H), 1H, NH], 2.15 (s, 3H, CH₃), 1.93 (s, 3H, CH₃), [1.70 (d, J=8.4 Hz, 1.48H), 1.68 (d, J=7.2 Hz, 1.56H), 3H, CH₃]; ¹⁹F NMR (376 MHz, CDCl₃) δ-74.8, -74.9; MS (EI) m/z (%) 501 (M+, 26.99), 120 (100); IR (neat): v=3335, 2972, 1579, 1557, 1510, 1482, 1451, 1417, 1375, 1357, 1327, 1248, 1206, 1171, 1136, 1091, 1073, 1016; the Anal. Calcd. for C₂₅H₂₂F₃N₃O₃S: C 59.87, H 4.42, N 8.38; found: C 59.85, H 4.58, N 8.29.

Example 4

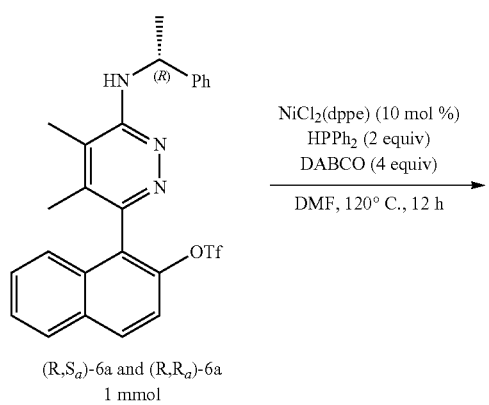

(R,S$_a$)-6a and (R,R$_a$)-6a
1 mmol

NiCl₂(dppe) (10 mol %)
HPPh₂ (2 equiv)
DABCO (4 equiv)
———————————→
DMF, 120° C., 12 h -continued

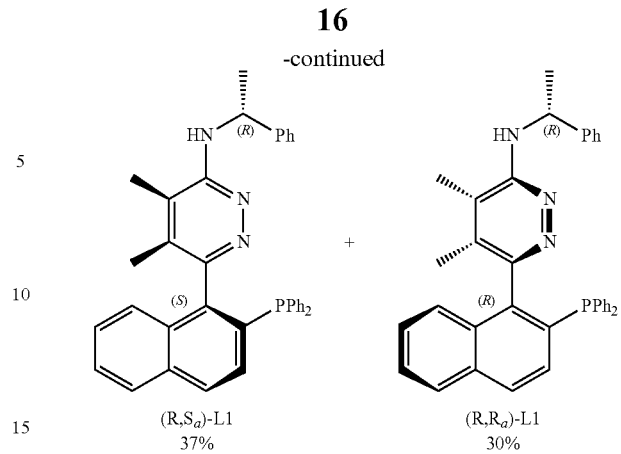

(R,S$_a$)-L1
37%

+

(R,R$_a$)-L1
30%

In an inert gas atmosphere, NiCl₂(dppe) (53.6 mg, 0.1 mmol)/DMF (2.4 mL) and diphenylphosphine (0.36 mL, d=1.07 g/mL, 0.3852 g, 2 mmol) were successively added to the dried reaction tube. The mixture of (R,S$_a$)-6a and (R,R$_a$)-6a (d.r.=1:1, 501.6 mg, 1 mmol) and DABCO (456.4 mg, 4 mmol) dissolved in 3.2 ml DMF were added to the reaction system with a syringe after stirring for 30 minutes in an oil bath preheated to 120° C. The mixed system reacted at 120° C. for 12 hours until the completion of reaction was confirmed by TLC detection. The mixture was cooled naturally to room temperature and directly depressurized to remove the solvent. Residue was subjected to column chromatography (eluent: toluene/ethyl acetate=40:1 (615 mL) to 20:1 (1050 mL); to toluene/acetone=10:1 (330 mL)) to obtain yellow solid foam (R,S$_a$)-L1 (198.6 mg, 37%, top spot) and yellow solid foam (R,R$_a$)-L1 (161.8 mg, 30%, bottom spot):

(R,S$_a$)-L1: melting point was 189.3-190.0° C. (toluene/n-hexane); [α]$_D^{25}$=-45.7 (c=0.995, CHCl₃); ¹H NMR (400 MHz, CDCl₃) δ 7.83 (d, J=8.0 Hz, 1H, ArH), 7.80 (d, J=8.8 Hz, 1H, ArH), 7.54-7.43 (m, 3H, ArH), 7.39-7.20 (m, 16H, ArH), 5.69 (quint, J=6.9 Hz, 1H, NCH), 4.41 (d, J=7.2 Hz, 1H, NH), 2.08 (s, 3H, CH₃), 1.73 (s, 3H, CH₃), 1.65 (d, J=6.8 Hz, 3H, CH₃); ¹³C NMR (100 MHz, CDCl₃) δ 155.9, 153.5, 153.48, 144.9, 143.7, 143.4, 137.8, 137.6, 137.1, 137.0, 135.3, 135.2, 134.7, 134.6, 133.9, 133.7, 133.5, 133.3, 133.1, 132.7, 132.6, 129.8, 128.4, 128.3, 128.2, 128.17, 128.1, 128.0, 127.8, 126.9, 126.7, 126.5, 126.4, 126.2, 120.3, 50.3, 22.5, 15.4, 11.7; ³¹P NMR (162 MHz, CDCl₃) δ-13.4; MS (ESI) m/z 538 ([M+H]⁺); IR (neat): v=3352, 3055, 3025, 2971, 2925, 1583, 1558, 1480, 1452, 1433, 1395, 1374, 1356, 1322, 1273, 1208, 1139, 1090, 1069, 1048, 1025; the Anal. Calcd. for C₃₆H₃₂N₃P: C 80.42, H 6.00, N 7.82; found: C 80.80, H 5.91, N 7.63;

(R,R$_a$)-L1: melting point was 111.3-111.9° C. (toluene/n-hexane); [α]$_D^{26}$=+104.7 (c=1.00, CHCl₃); ¹H NMR (400 MHz, CDCl₃) δ 7.80 (d, J=8.4 Hz, 1H, ArH), 7.77 (d, J=8.8 Hz, 1H, ArH), 7.52-7.40 (m, 3H, ArH), 7.37-7.15 (m, 16H, ArH), 5.64 (quint, J=6.5 Hz, 1H, NCH), 4.47 (d, J=6.8 Hz, 1H, NH), 1.98 (s, 3H, CH₃), 1.72 (s, 3H, CH₃), 1.64 (d, J=6.4 Hz, 3H, CH₃); ¹³C NMR (100 MHz, CDCl₃) δ 155.9, 153.5, 153.4, 144.8, 143.5, 143.2, 137.7, 137.6, 136.7, 136.6, 135.12, 135.10, 134.9, 134.8, 133.6, 133.5, 133.44, 133.40, 133.3, 132.6, 132.5, 129.7, 128.4, 128.2, 128.11, 128.10, 128.0, 127.8, 126.9, 126.6, 126.4, 126.3, 126.0, 126.0, 120.4, 50.5, 22.2, 15.4, 11.7; ³¹P NMR (162 MHz, CDCl₃) δ-12.2; MS (ESI) m/z 538 ([M+H]⁺); IR (neat): v=3330, 3053, 2968, 2923, 1582, 1555, 1479, 1449, 1433, 1373, 1354, 1320, 1207, 1177, 1140, 1111, 1089, 1069, 1025; the Anal. Calcd. for $C_{36}H_{32}N_3P$: C 80.42, H 6.00, N 7.82; found: C 80.27, H 6.00, N 7.79.

Example 5

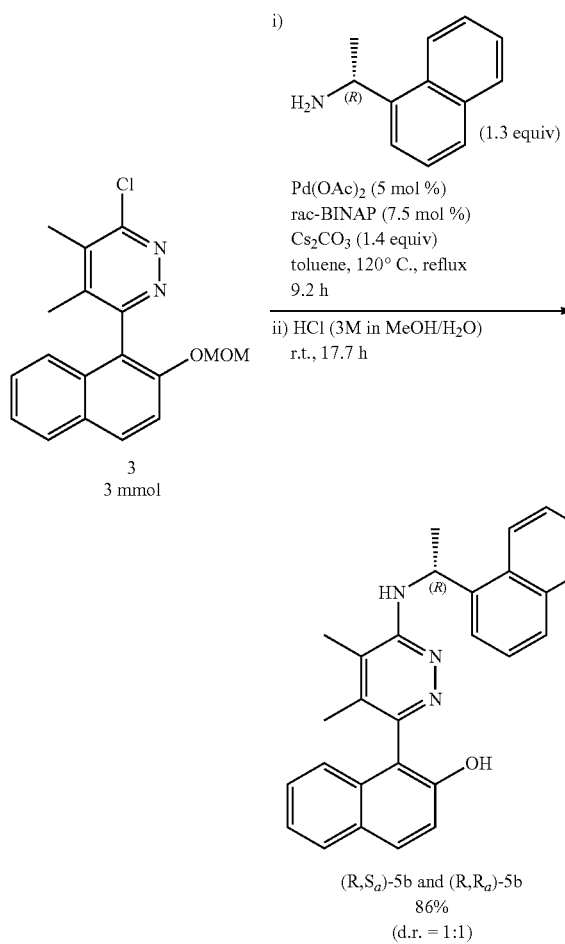

Pd(OAc)$_2$ (34.1 mg, 0.15 mmol), racemate 1,1'-binaphthaline-2,2'-bisdiphenylphosphine (143.8 mg, 0.225 mmol), and toluene (3 mL) were successively added to a dry reaction flask with a reflux condenser under inert gas protection. After stirring at room temperature for 30 minutes, 3 (988.3 mg, 3 mmol), (R)-1-(1-naphthyl)-1-ethylamine (0.63 mL, d=1.067 g/mL, 0.6722 g, 3.9 mmol)/toluene (3 mL) and Cs$_2$CO$_3$ (1.3711 g, 4.2 mmol) were successively added. The mixture was stirred in an oil bath preheated to 120° C. and refluxed for 9.2 hours until the completion of the reaction was confirmed by TLC detection. The mixture was removed from the oil bath, cooled naturally to room temperature, filtered by a short alkaline aluminum oxide column (200-300 mesh) and rinsed with 60 mL ethyl acetate. The filtrate was concentrated and subjected to column chromatography (eluent: petroleum ether/ethyl acetate=5:1 (1200 mL) to 4:1 (750 mL) to 2:1 (300 mL)) to obtain the yellow solid foam crude product, which was directly used for the next step.

The crude product obtained in the previous step and 48.7 mL HCl (mixed solution of 3 M MeOH/H$_2$O) were added to the reaction flask. The mixture was stirred at room temperature for 17.7 hours until the completion of reaction was confirmed by TLC detection. The mixture was neutralized to neutral by concentrate ammonia, diluted by 30 mL water and extracted with 3×50 mL dichloromethane. The organic phases were combined, dried by anhydrous sodium sulfate, filtered, concentrated and subjected to column chromatography (eluent: petroleum ether/ethyl acetate=4:1 (1750 mL) to 3:1 (400 mL) to dichloromethane/methanol=20:1 (630 mL)) to obtain the mixture of yellow solid foam (R,S$_a$)-5b and (R,R$_a$)-5b (1.0834 g, 86%, d.r.=1:1) (d.r. value of the product was determined by nuclear magnetic analysis): melting point was 207.9-208.5° C. (ethyl acetate/petroleum ether); $^1$H NMR (400 MHz, CDCl$_3$) δ 8.28-8.16 (m, 1H, ArH), 7.91-7.39 (m, 8H, protons from ArH and OH), 7.32-7.01 (m, 5H, protons from ArH and OH), 6.44-6.30 (m, 1H, NCH), [4.61 (d, J=6.4 Hz, 0.48H), 4.57 (d, J=6.8 Hz, 0.47H), 1H, NH], [1.94 (s, 1.51H), 1.92 (s, 1.38H), 3H, CH$_3$], 1.84-1.73 (6H, 2×CH$_3$); MS (ESI) m/z 420 ([M+H]$^+$); IR (neat): v=3356, 3046, 2963, 2927, 2926, 1621, 1583, 1556, 1510, 1484, 1441, 1366, 1344, 1270, 1239, 1210, 1180, 1142, 1081, 1012; HRMS calcd for $C_{28}H_{26}N_3O$ ([M+H]$^+$): 420.2070; found: 420.2071.

Example 6

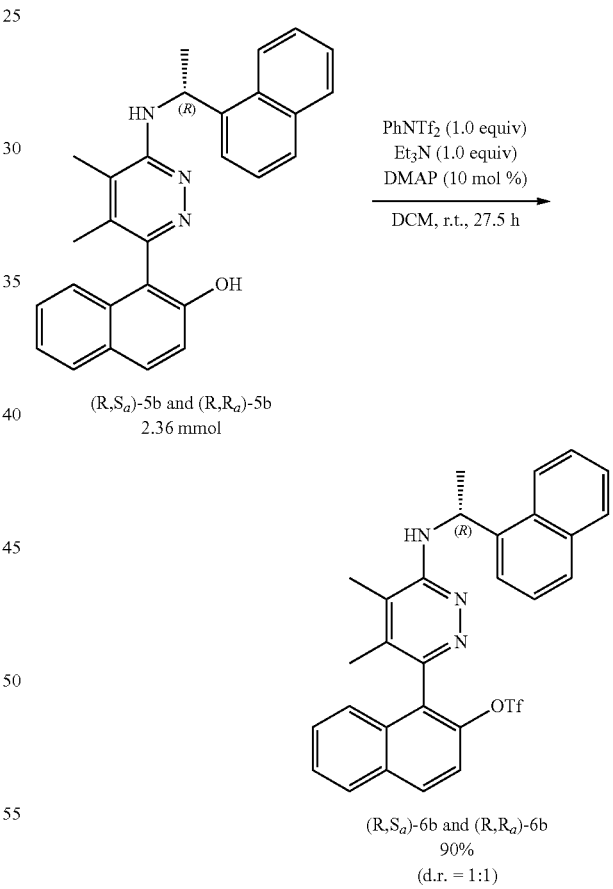

The mixture of (R,S$_a$)-5b and (R,R$_a$)-5b (d.r.=1:1, 993.9 mg, 2.36 mmol) and 4-dimethylaminopyridine (29.8 mg, 0.24 mmol) were added to the reaction flask. The Ar was replaced from the reaction bottle three times and 23.6 mL DCM, Et$_3$N (0.33 mL, d=0.728 g/mL, 0.2402 g, 2.36 mmol), and N-phenylbis (trifluoromethanesulfonyl) imide (861.7 mg, 2.36 mmol) were successively added. The mixture was stirred at room temperature for 27.5 h until the completion of reaction was confirmed by TLC detection. The mixture was directly concentrated and subjected to column chromatography (eluent: petroleum ether/ethyl acetate=10:1 (330 mL) to 5:1 (1920 mL)) to obtain a mixture of yellow solid foam (R,S$_a$)-6b and (R,R$_a$)-6b (1.1909 g, 90%, d.r.=1:1) (d.r. value of the product was determined by nuclear magnetic analysis): melting point was 103.5-104.5° C. (as crystals cannot be obtained by recrystallization, melting point was achieved by direct measuring of solids obtained by spin-drying); $^1$H NMR (400 MHz, CDCl$_3$) δ [8.32 (d, J=8.0 Hz, 0.49H), 8.18-8.13 (m, 0.51H), 1H, ArH], 8.00 (d, J=9.2 Hz, 1H, ArH), [7.94 (d, J=8.4 Hz, 0.5H), 7.93 (d, J=8.0 Hz, 0.5H), 1H, ArH], 7.90-7.84 (m, 1H, ArH), 7.82 (d, J=8.0 Hz, 1H, ArH), [7.69 (d, J=7.2 Hz, 0.52H), 7.65 (d, J=7.2 Hz, 0.52H), 1H, ArH], 7.59-7.43 (m, 7H, ArH), 6.59-6.47 (m, 1H, NCH), [4.57 (d, J=8.0 Hz, 0.50H), 4.55 (d, J=8.4 Hz, 0.49H), 1H, NH], [2.07 (s, 1.48H), 2.02 (s, 1.48H), 3H, CH$_3$], [1.92 (s, 1.50H), 1.92 (s, 1.50H), 3H, CH$_3$], [1.88 (d, J=6.4 Hz, 1.51H), 1.84 (d, J=6.4 Hz, 1.48H), 3H, CH$_3$]; $^{19}$F NMR (376 MHz, CDCl$_3$) δ-74.8, -74.9; MS (ESI) m/z 552 ([M+H]$^+$); IR (neat): v=3353, 3049, 2974, 1579, 1556, 1510, 1463, 1448, 1417, 1373, 1327, 1247, 1205, 1171, 1135, 1073, 1015; the Anal. Calcd. for C$_{29}$H$_{24}$F$_3$N$_3$O$_3$S: C 63.15, H 4.39, N 7.62; found: C 62.93, H 4.39, N 7.46.

Example 7

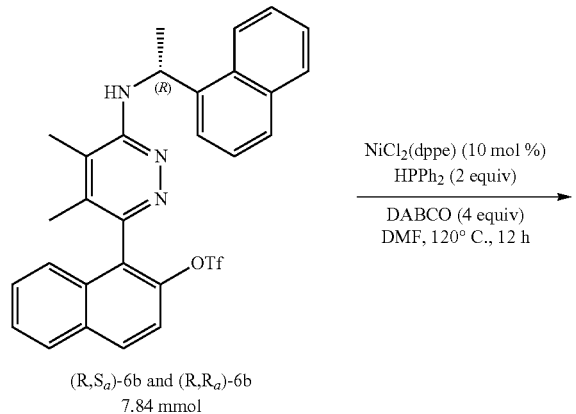

(R,S$_a$)-6b and (R,R$_a$)-6b
7.84 mmol

NiCl$_2$(dppe) (10 mol %)
HPPh$_2$ (2 equiv)
DABCO (4 equiv)
DMF, 120° C., 12 h

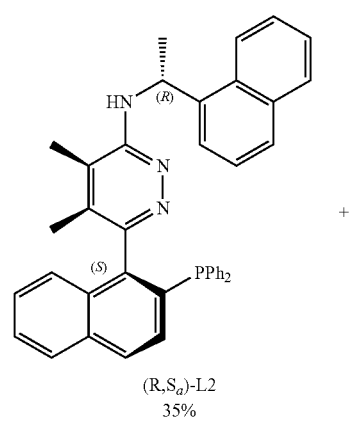

(R,S$_a$)-L2
35%

+

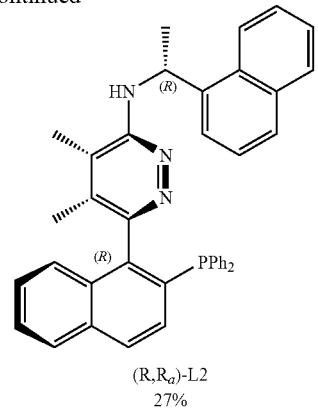

(R,R$_a$)-L2
27%

In an inert gas atmosphere, NiCl$_2$(DPPE) (421.3 mg, 0.79 mmol) and diphenylphosphine (2.81 mL, d=1.07 g/mL, 3.0067 g, 15.68 mmol)/DMF (18.8 mL) were successively added to the dried reaction tube. The mixture of (R,S$_a$)-6b and (R,R$_a$)-6b (d.r.=1:1, 4.3186 g, 7.84 mmol) and DABCO (3.5635 g, 31.36 mmol) dissolved in 25.1 mL DMF were added to the reaction system with a syringe after stirring for 30 minutes in an oil bath preheated to 120° C. until the completion of reaction was confirmed by TLC detection. Cooled naturally to room temperature, the mixture is directly depressurized to remove the solvent. Residue was subjected to column chromatography (eluent: toluene/ethyl acetate=40:1 (2050 mL); to toluene/acetone=10:1 (330 mL)) to obtain yellow solid foam (R,S$_a$)-L2 (1.6234 g, 35%, top point) and yellow solid foam (R,R$_a$)-L2 (1.2287 g, 27%, bottom point):

(R,S$_a$)-L2: melting point was 211.4-212.0° C. (toluene/n-hexane); [α]$_D^{25}$=-65.0 (c=1.00, CHCl$_3$); $^1$H NMR (400 MHz, CDCl$_3$) δ 8.32 (d, J=7.2 Hz, 1H, ArH), 7.90-7.77 (m, 4H, ArH), 7.68 (d, J=6.8 Hz, 1H, ArH), 7.54-7.45 (m, 4H, ArH), 7.40-7.19 (m, 13H, ArH), 6.52 (quint, J=7.2 Hz, 1H, NCH), 4.44 (d, J=7.2 Hz, 1H, NH), 2.00 (s, 3H, CH$_3$), 1.82 (d, J=6.4 Hz, 3H, CH$_3$), 1.74 (s, 3H, CH$_3$); $^{13}$C NMR (100 MHz, CDCl$_3$) δ 155.7, 153.5, 153.4, 143.7, 143.3, 140.3, 137.8, 137.6, 137.1, 136.9, 135.29, 135.26, 134.8, 134.7, 133.9, 133.8, 133.7, 133.5, 133.4, 133.2, 132.7, 132.6, 131.4, 129.8, 128.5, 128.4, 128.3, 128.2, 128.18, 128.11, 128.05, 127.84, 127.77, 126.6, 126.4, 126.2, 126.1, 125.6, 125.2, 124.0, 122.4, 120.3, 46.4, 21.1, 15.4, 11.7; $^{31}$P NMR (162 MHz, CDCl$_3$) δ-13.1; MS (ESI) m/z 588 ([M+H]$^+$); IR (neat): v=3365, 3051, 3000, 2971, 2923, 1584, 1562, 1480, 1457, 1433, 1395, 1373, 1363, 1313, 1241, 1179, 1143, 1088, 1069, 1026; the Anal. Calcd. for C$_{40}$H$_{34}$N$_3$P: C 81.75, H 5.83, N 7.15; found: C 81.56, H 5.73, N 7.04; (R,R$_a$)-L2: melting point was 128.2-128.8° C. (toluene/n-hexane); [α]$_D^{26}$=+129.5 (c=1.00, CHCl$_3$); $^1$H NMR (400 MHz, CDCl$_3$) δ 8.31-8.23 (m, 1H, ArH), 7.91-7.79 (m, 4H, ArH), 7.68 (d, J=7.2 Hz, 1H, ArH), 7.54-7.45 (m, 4H, ArH), 7.41-7.21 (m, 13H, ArH), 6.47 (quin t, J=6.4 Hz, 1H, NCH), 4.45 (d, J=7.2 Hz, 1H, NH), 1.98 (s, 3H, CH$_3$), 1.86 (d, J=6.8 Hz, 3H, CH$_3$), 1.74 (s, 3H, CH$_3$); $^{13}$C NMR (100 MHz, CDCl$_3$) δ 155.7, 153.42, 153.36, 143.4, 143.1, 140.1, 137.8, 137.6, 136.7, 136.6, 135.24, 135.22, 135.19, 135.07, 133.8, 133.73, 133.66, 133.5, 133.4, 133.3, 132.6, 132.5, 131.4, 129.6, 128.5, 128.2, 128.13, 128.06, 127.9, 127.8, 126.6, 126.4, 126.2, 126.0, 125.6, 125.2, 124.0, 122.4, 120.4, 46.4, 20.9, 15.4, 11.6; $^{31}$P NMR (162 MHz, CDCl$_3$) δ-12.6; MS (ESI) m/z 588 ([M+H]$^+$); IR (neat): v=3329, 3049, 2969, 2923, 1582, 1555, 1505, 1479, 1456, 1435, 1371, 1319, 1236, 1176, 1131, 1118, 1093, 1069, 1025; the Anal. Calcd. for $C_{40}H_{34}N_3P$: C 81.75, H 5.83, N 7.15; found: C 81.87, H 5.90, N 7.08.

Example 8

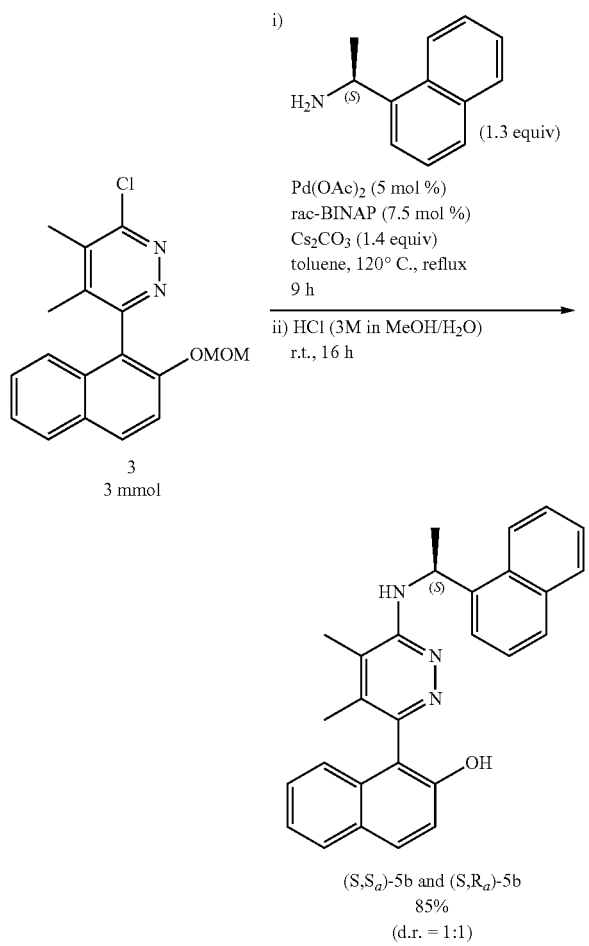

Pd(OAc)$_2$ (34.3 mg, 0.15 mmol), racemate 1,1'-binaphthalene-2,2'-bisdiphenylphosphine (143.1 mg, 0.225 mmol) and toluene (3 mL) were successively added to a dry reaction flask with a reflux condenser under inert gas protection. After stirring at room temperature for 30 minutes, 3 (986.8 mg, 3 mmol), (S)-1-(1-naphthyl)-1-ethylamine (0.63 mL, d=1.067 g/mL, 0.6722 g, 3.9 mmol)/toluene (3 mL) and Cs$_2$CO$_3$ (1.3710 g, 4.2 mmol) were successively added. The mixture was stirred in an oil bath preheated to 120° C. and refluxed for 9 h until the completion of the reaction was confirmed by TCL detection. The mixture was removed from the oil bath, cooled naturally to room temperature and filtered by a short alkaline aluminum oxide column (200-300 mesh) and rinsed with 60 mL ethyl acetate. The filtrate was concentrated and subjected to column chromatography (eluent: petroleum ether/ethyl acetate=5:1 (1200 mL) to 4:1 (750 mL) to 2:1 (300 mL)) to obtain the yellow solid foam crude product, which was directly used for the next step.

The crude product obtained in the previous step and 48.7 mL HCl (mixed solution of 3 M MeOH/H$_2$O) was added to the reaction flask. The mixture was stirred at room temperature for 16 hours until the completion of the reaction confirmed by TLC. The mixture was neutralized to neutral by concentrate ammonia, diluted with 30 mL water and extracted with 3×50 mL dichloromethane. The organic phases were combined, dried by anhydrous sodium sulfate, filtered, concentrated and subjected to column chromatography (eluent: petroleum ether/ethyl acetate=4:1 (1750 mL) to 3:1 (400 mL) to dichloromethane/methanol=20:1 (420 mL)) to obtain the mixture of yellow solid foam (R,S$_a$)-5b and (R,R$_a$)-5b (1.0753 g, 85%, d.r.=1:1) (d.r. value of the product was determined by nuclear magnetic analysis); $^1$H NMR (400 MHz, CDCl$_3$) δ 8.28-8.16 (m, 1H, ArH), 7.91-7.39 (m, 8H, protons from ArH and OH), 7.32-7.01 (m, 5H, protons from ArH and OH), 6.44-6.30 (m, 1H, NCH), [4.61 (d, J=6.4 Hz, 0.48H), 4.57 (d, J=6.8 Hz, 0.47H), 1H, NH], [1.94 (s, 1.51H), 1.92 (s, 1.38H), 3H, CH$_3$], 1.84-1.73 (6H, 2×CH$_3$)

Example 9

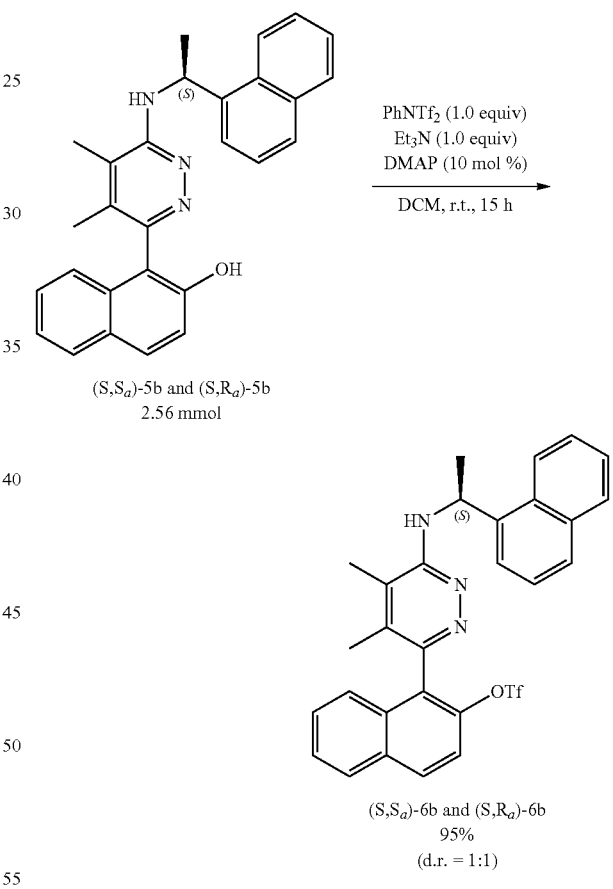

The mixture of (S,S$_a$)-5b and (S,R$_a$)-5b (d.r.=1:1, 1.0753 g, 2.56 mmol) and 4-dimethylaminopyridine (31.9 mg, 0.256 mmol) were added to the reaction flask. The Ar was replaced from the reaction bottle three times and 25.6 mL DCM, Et$_3$N (0.36 mL, d=0.728 g/mL, 0.2402 g, 2.56 mmol), and N-phenylbis (trifluoromethanesulfonyl) imide (933.87 mg, 2.56 mmol) were successively added. The mixture was stirred at room temperature for 15 hours until the completion of reaction was confirmed by TCL detection. The mixture was directly concentrated and subjected to column chromatography (eluent: petroleum ether/ethyl acetate=10:1 (330 mL) to 5:1 (600 mL)) to obtain a mixture of yellow solid foam (R,$S_a$)-6b and (R,$R_a$)-6b (1.3457 g, 90%, d.r.=1:1) (d.r. value of the product was determined by nuclear magnetic analysis): $^1$H NMR (400 MHz, CDCl$_3$) δ [8.32 (d, J=8.0 Hz, 0.49H), 8.18-8.13 (m, 0.51H), 1H, ArH], 8.00 (d, J=9.2 Hz, 1H, ArH), [7.94 (d, J=8.4 Hz, 0.5H), 7.93 (d, J=8.0 Hz, 0.5H), 1H, ArH], 7.90-7.84 (m, 1H, ArH), 7.82 (d, J=8.0 Hz, 1H, ArH), [7.69 (d, J=7.2 Hz, 0.52H), 7.65 (d, J=7.2 Hz, 0.52H), 1H, ArH], 7.59-7.43 (m, 7H, ArH), 6.59-6.47 (m, 1H, NCH), [4.57 (d, J=8.0 Hz, 0.50H), 4.55 (d, J=8.4 Hz, 0.49H), 1H, NH], [2.07 (s, 1.48H), 2.02 (s, 1.48H), 3H, CH$_3$], [1.92 (s, 1.50H), 1.92 (s, 1.50H), 3H, CH$_3$], [1.88 (d, J=6.4 Hz, 1.51H), 1.84 (d, J=6.4 Hz, 1.48H), 3H, CH$_3$]; $^{19}$F NMR (376 MHz, CDCl$_3$) δ-74.8, -74.9.

Example 10

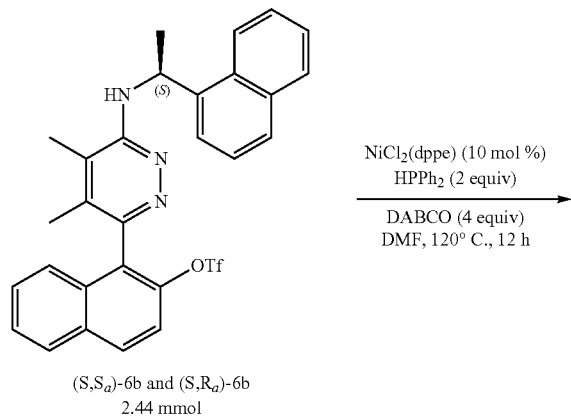

In an inert gas atmosphere, NiCl$_2$(dppe) (131.9 mg, 0.244 mmol) and diphenylphosphine ((0.88 mL, d=1.07 g/mL, 3.0067 g, 4.88 mmol)/DMF (5.9 mL) were successively added to the dried reaction tube. The mixture of (R,$S_a$)-6b and (R,$R_a$)-6b (d.r.=1:1, 1.3457 g, 2.44 mmol) and DABCO (1.1097 g, 9.76 mmol) of dissolved in 5.9 mL DMF were added to the reaction system with a syringe after stirring for 30 minutes in an oil bath preheated to 120° C. until the completion of reaction was confirmed by TLC detection. Cooled naturally to room temperature, the mixture is directly depressurized to remove the solvent. Residue was subjected to column chromatography (eluent: toluene/ethyl acetate=40:1 (1600 mL); to toluene/acetone=10:1 (330 mL)) to obtain yellow solid foam (R,$S_a$)-L2 (0.4819 g, 34%, top point) and yellow solid foam (S,$S_a$)-L2 (0.3753 g, 26%, bottom point):

(S,$R_a$)-L2: $^1$H NMR (400 MHz, CDCl$_3$) δ 8.32 (d, J=7.2 Hz, 1H, ArH), 7.90-7.77 (m, 4H, ArH), 7.68 (d, J=6.8 Hz, 1H, ArH), 7.54-7.45 (m, 4H, ArH), 7.40-7.19 (m, 13H, ArH), 6.52 (quint, J=7.2 Hz, 1H, NCH), 4.44 (d, J=7.2 Hz, 1H, NH), 2.00 (s, 3H, CH$_3$), 1.82 (d, J=6.4 Hz, 3H, CH$_3$), 1.74 (s, 3H, CH$_3$); $^{31}$P NMR (162 MHz, CDCl$_3$) δ-13.1.

(S,$S_a$)-L2: $^1$H NMR (400 MHz, CDCl$_3$) δ 8.31-8.23 (m, 1H, ArH), 7.91-7.79 (m, 4H, ArH), 7.68 (d, J=7.2 Hz, 1H, ArH), 7.54-7.45 (m, 4H, ArH), 7.41-7.21 (m, 13H, ArH), 6.47 (quint, J=6.4 Hz, 1H, NCH), 4.45 (d, J=7.2 Hz, 1H, NH), 1.98 (s, 3H, CH$_3$), 1.86 (d, J=6.8 Hz, 3H, CH$_3$), 1.74 (s, 3H, CH$_3$). $^{31}$P NMR (162 MHz, CDCl$_3$) δ-12.6.

Example 11

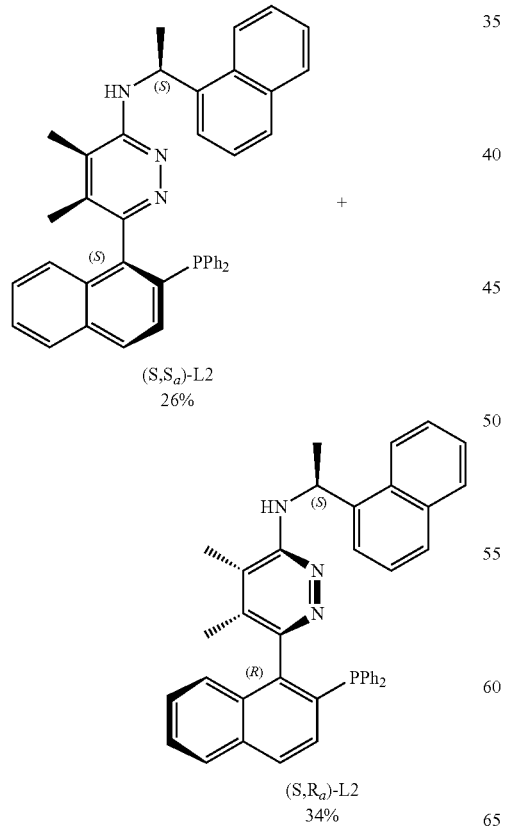

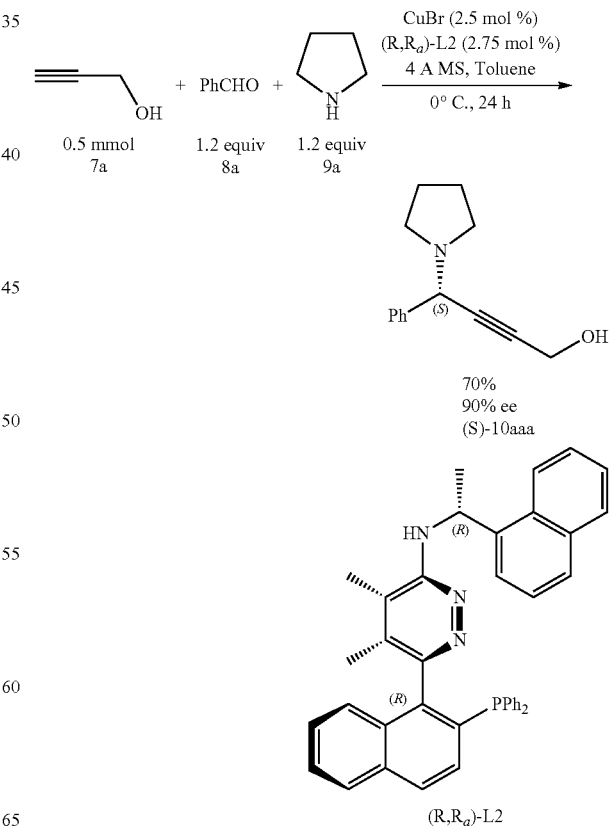

CuBr (1.8 mg, 0.0125 mmol), (R,R$_a$)-L2 (8.1 mg, 0.01375 mmol), 4 Å molecular sieve (150.5 mg), and toluene (0.75 mL) were added to the dried tubes in an inert atmosphere. After 30 minutes at room temperature, propargyl alcohol 7a (28.0 mg, 0.5 mmol) and benzaldehyde 8a (63.7 mg, 0.6 mmol)/toluene (0.5 mL) were successively added. The mixture was stirred at 0° C. for 10 minutes, than tetrahydropyrrole 9a (42.7 mg, 0.6 mmol) was added. The mixture reacted at 0° C. for 24 hours until the completion of reaction was confirmed by TCL detection. The reaction mixture was filtered by a short alkaline alumina trioxide column (200-300 mesh) and eluted with 44 mL dichloromethane/MeOH (10:1). The mixture was spun dry and subjected to column chromatography (eluent: petroleum ether/ethyl acetate=2:1) to obtain liquid chiral propargyl amine product (S)-10aaa (74.9 mg, 70%): 90% EE (HPLC testing conditions: Chiralcel OD-H column, n-hexane/isopropanol=95/5, 1.2 mL min-1, λ=214 nm, $t_R$(large peak)=10.1 min, $t_R$(small peak)=7.7 min; $[α]^3$=−28.1 (c=1.05, CHCl$_3$); $^1$H NMR (400 MHz, CDCl$_3$) δ 7.51 (d, J=7.2 Hz, 2H, ArH), 7.33 (t, J=7.2 Hz, 2H, ArH), 7.27 (t, J=6.4 Hz, 1H, ArH), 4.62 (s, 1H, CH), 4.36 (d, J=1.6 Hz, 2H, OCH$_2$), 2.67-2.51 (m, 4H, 2×NCH$_2$), 2.04 (br, 1H, OH), 1.83-1.71 (m, 4H, 2×CH$_2$); 13C NMR (100 MHz, CDCl$_3$) δ 138.9, 128.24, 128.21, 127.7, 85.0, 82.7, 58.9, 50.9, 50.5, 23.2; MS (EI) m z (%) 215 (M+, 20.49), 138 (100); IR (neat): v=3065, 2960, 2924, 2871, 2841, 2729, 1489, 1455, 1372, 1345, 1309, 1270, 1233, 1206, 1121, 1087, 1074, 1033, 1024 cm-1; HRMS calcd for C$_{14}$H$_{18}$NO ([M+H]$^+$): 216.1383, found: 216.1381.

Example 12

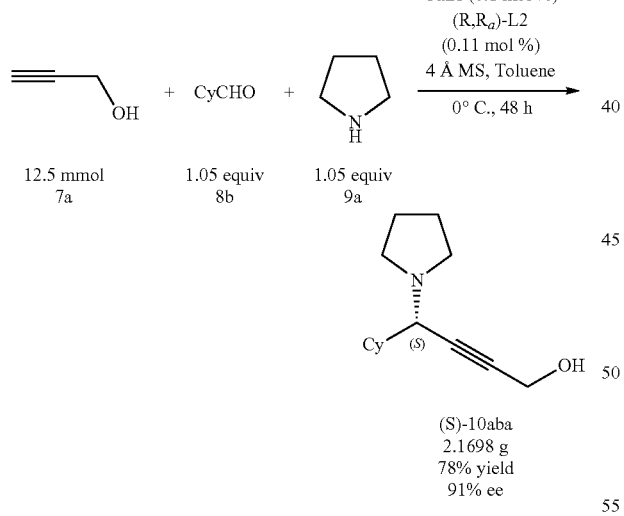

(S)-10aba
2.1698 g
78% yield
91% ee

CuBr (1.8 mg, 0.0125 mmol), (R,R$_a$)-L2 (8.1 mg, 0.01375 mmol), 4 Å molecular sieve (1.8915 g), and toluene (10 mL) were added to the dried tubes in an inert atmosphere. After stirring at room temperature for 1 h, propargyl alcohol 7a (0.7018 g, 12.5 mmol)/toluene (7 mL) and 8b (1.4829 g, 13.1 mmol)/toluene (7 mL) were successively added. The mixture was stirred at 0° C. for 10 minutes, than tetrahydropyrrole 9a (0.9371 g, 13.1 mmol)/toluene (7 mL) were added. The mixture was stirred at 0° C. for 48 hours until the completion of reaction was confirmed by TCL detection. The reaction mixture was filtered by a short alkaline alumina trioxide column (200-300 mesh) and rinsed with 110 mL dichloromethane/MeOH (10:1, 110 mL). The mixture was spun dry and the residue was dissolved in 30 mL dichloromethane and washed with 30 mL saturated NaCl aqueous solution. Organic phase was extracted with 3×25 mL 1 M hydrochloric acid. The water phases were combined, neutralized with concentrated ammonia water and extracted with 3×50 mL diethyl ether. The organic phases were combined, dried with anhydrous sodium sulfate, filtered and spun dry to obtain pure liquid propargyl amine (S)-10aba (2.1698 g, 78%): 91% ee [In previous literature reports (Chem. Coummun. 2013, 49, 10175), the best result was 84% ee value, indicating that the new ligand prepared by the present invention had better stereochemical control effect. In addition, in the example of the invention, the catalyst dosage was only 0.1 mol %, and the corresponding chiral propargyl amine compound was synthesized at the gram level without column chromatography separation and purification, which had a good prospect of industrial application.](HPLC test conditions: Chiralcel AD-H column, n-hexane/isopropanol=95/5, 0.8 mL min-1, λ=214 nm, $t_R$(large peak)=8.8 min, $t_R$(small peak)=7.5 min); $^1$H NMR (400 MHz, CDCl$_3$) δ 4.31 (d, J=1.6 Hz, 2H, OCH$_2$), 3.15 (d, J=8.0 Hz, 1H, NCH), 2.74-2.60 (m, 2H, NCH$_2$), 2.59-2.47 (m, 2H, NCH$_2$), 2.06-1.60 (m, 10H), 1.56-1.40 (m, 1H), 1.31-0.96 (m, 5H); $^{13}$C NMR (100 MHz, CDCl$_3$) δ 84.1, 83.1, 60.9, 50.8, 50.1, 41.0, 30.5, 29.7, 26.5, 26.1, 26.0, 23.2.

Example 13

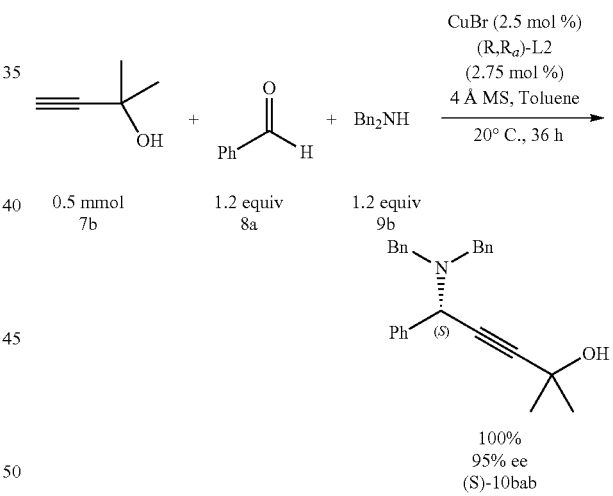

100%
95% ee
(S)-10bab

Operation were conducted by referring to Example 8. CuBr (1.8 mg, 0.0125 mmol), (R,R$_a$)-L2 (8.1 mg, 0.01375 mmol), 4 Å molecular sieve (150.5 mg) and toluene (0.75 mL), acetylene 7b (43.2 mg, 0.5 mmol), benzaldehyde 8a (63.6 mg, 0.6 mmol) and toluene (0.5 mL), and dibenzylamine 9b (120.5 mg, 0.6 mmol) reacted at 20° C. for 26 hours. The mixture was subjected to column chromatography (eluent: petroleum ether/ethyl acetate=20:1 to 10:1) to obtain chiral propargyl amine compound (S)-10bab (186.1 mg, 100%): 95% ee [In the previous literature (J Org. Chem. 2019, 84, 5763.), the best results were 49% yield and 32% ee value, indicating that the novel ligand prepared by the present invention has excellent catalytic activity and stereochemical control effect.](HPLC test conditions: Chiralcel OD-H column, n-hexane/isopropanol=100/1, 1.2 mL min-1, λ=214 nm, t_R(large peak)=15.8 min, t_R(small peak)=17.8 min); [c]=−65.2 (c=1.025, CHCl$_3$); $^1$H NMR (400 MHz, CDCl$_3$) δ 7.63 (d J=8.0 Hz, 2H, ArH), 7.39 (d, J=7.2 Hz, 4H, ArH), 7.36-7.28 (m, 6H, ArH), 7.27-7.19 (m, 3H, ArH), 4.72 (s, 1H, NCH), 3.71 (d, J=13.2 Hz, 2H, 2×one proton from NCH$_2$), 3.40 (d, J=13.6 Hz, 2H, 2×one proton from NCH$_2$), 2.09 (br, 1H, OH), 1.71 (s, 6H, 2×CH$_3$); $^{13}$C NMR (100 MHz, CDCl$_3$) δ 139.4, 139.0, 128.8, 128.2, 128.1, 128.0, 127.4, 127.0, 93.6, 76.9, 65.5, 55.3, 54.5, 32.0; MS (ESI) m z 370 ([M+H]$^+$); IR (neat): v=3358, 3085, 3061, 3028, 2979, 2930, 2832, 2807, 1602, 1493, 1451, 1362, 1327, 1274, 1232, 1165, 1116, 1070, 1028; HRMS calcd for C$_{26}$H$_{28}$NO ([M+H]$^+$): 370.2165, Found: 370.2170.

The above-mentioned embodiments are only to illustrate the technical concept and features of the present invention, and their purpose is to enable the technical personnel in the field to understand the contents of the invention and implement them, and it shall not limit the scope of protection of the invention. All equivalent changes or modifications made according to the essence of the present invention are all covered by the protection scope of the present invention.

What is claimed:

1. A class of phosphine nitrogen ligand with multiple chiral centers, wherein, the structures are as formulas L1 or L2:

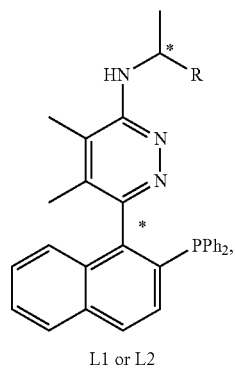

L1 or L2 wherein,

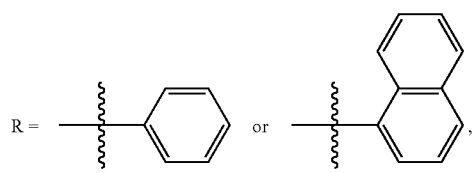

* represents the chiral center.

2. The ligand of claim 1, wherein, it includes the following structural formulas:

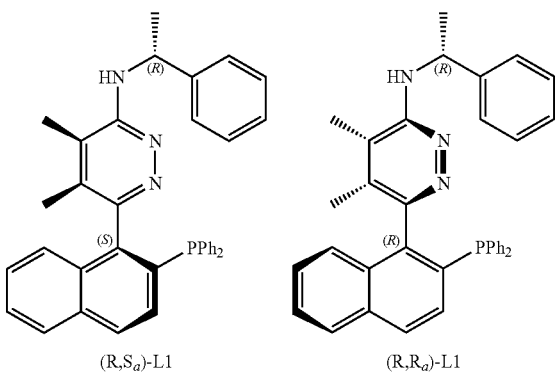

(R,S$_a$)-L1        (R,R$_a$)-L1

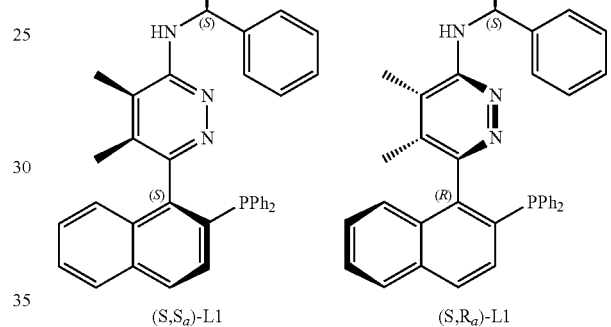

(S,S$_a$)-L1        (S,R$_a$)-L1

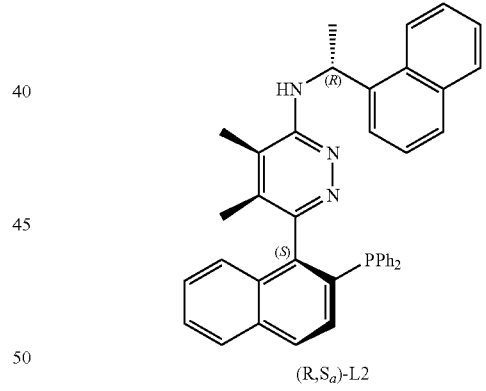

(R,S$_a$)-L2

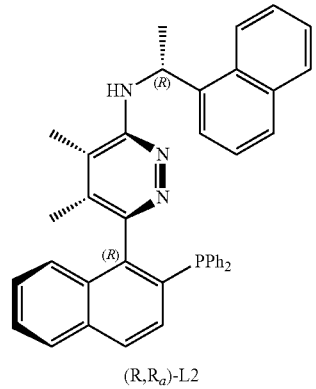

(R,R$_a$)-L2

-continued

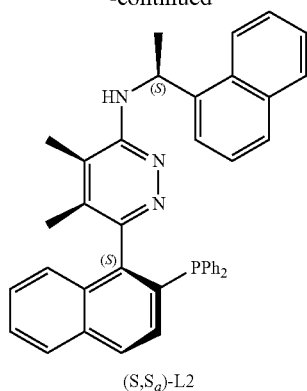

(S,S<sub>a</sub>)-L2

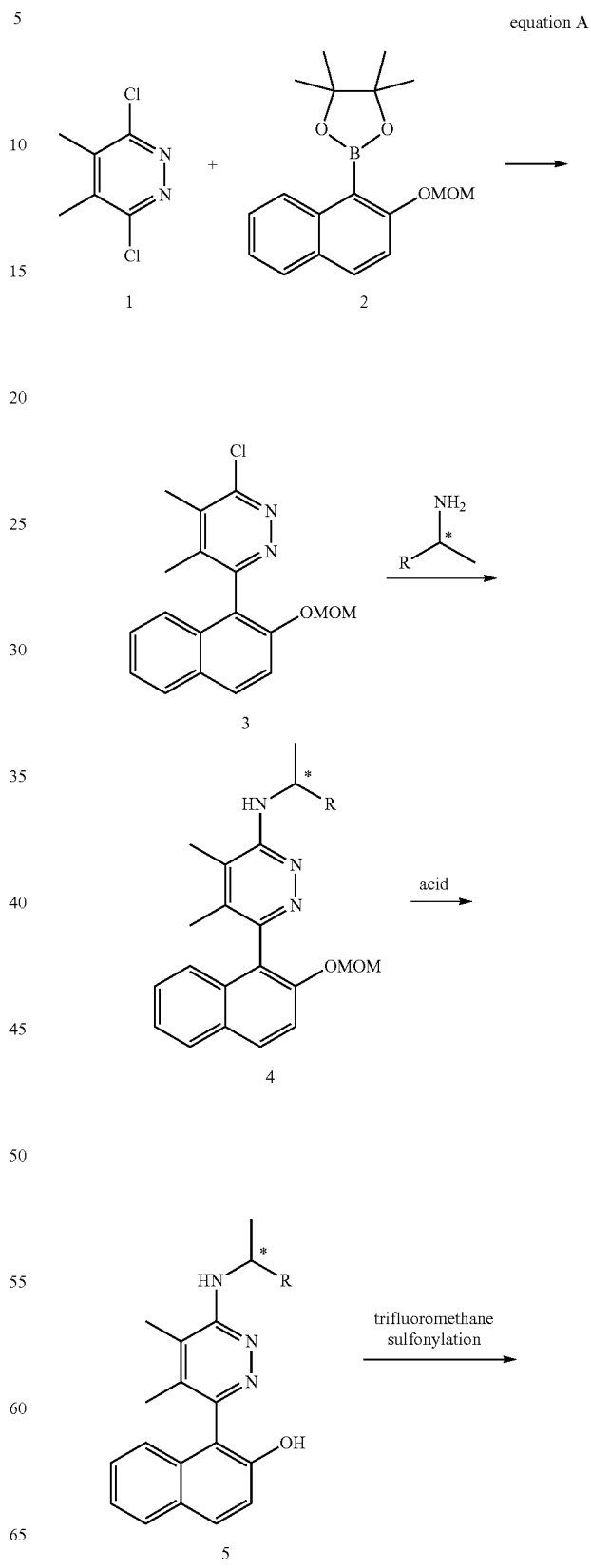

the reaction process has the following reaction equation (A):

3. A method for the synthesis of a class of phosphine nitrogen ligand with multiple chiral centers, wherein, the phosphine nitrogen ligand is obtained by the following steps:
    (1) in the solvent, 3,6-dichloro-4,5-dimethylpyridazine and borate ester compounds are taken as raw materials to react to obtain the biaryl compounds, in the presence of base, with palladium salt and phosphine ligand as catalytic system or directly using palladium and phosphine complexes;
    (2) in the solvent, the biaryl compounds obtained in step (1) and chiral amine are taken as raw materials, in the presence of a base, with palladium salt and phosphine ligand as catalytic system or directly using palladium and phosphine complexes to obtain the amination product through coupling reaction;
    (3) in the solvent, the amination product obtained in step (2) reacts with the acid to obtain the phenolic products;
    (4) in an organic solvent, in the presence of an acid binding agent, the phenolic products obtained in step (3), trifluoromethanesulfonation reagent and 4-dimethylaminopyridine react to obtain the trifluoromethanesulfonation products;
    (5) in an organic solvent, the trifluoromethanesulfonation product obtained in step (4), diphenylphosphine, nickel and an organic base react to obtain the phosphine nitrogen ligand with multiple chiral centers;

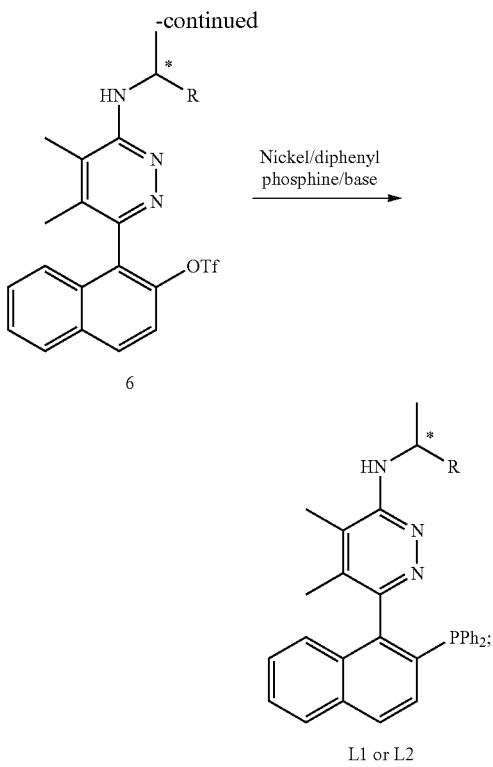

wherein,

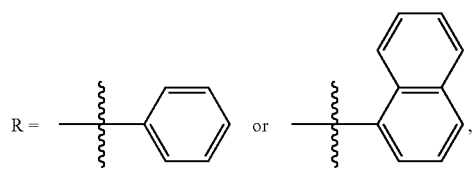

represents the chiral centers.

4. The method of claim 3, wherein, in step (1), the molar ratio of the said 3,6-dichloro-4,5-dimethylpyridazine:borate ester compound:base:palladiumsalt:phosphine ligand is 1:(1~2):(1~2):(0.01~0.2):(0.01~0.4); and/or, the molar ratio of the said 3,6-dichloro-4,5-dimethylpyridazine:borate ester compound:base:palladium and phosphine complex is 1:(1~2):(1~2):(0.01~0.2); and/or, the said base is one or more of sodium bicarbonate, sodium carbonate, sodium hydroxide, potassium bicarbonate, potassium carbonate, potassium hydroxide, potassium phosphate, cesium fluoride or cesium carbonate; and/or, the said palladium salts are one or more of palladium acetate, palladium chloride, palladium dibenzylidenyl acetone, cinnamyl palladium chloride, allyl palladium chloride, palladium trifluoroacetate, palladium diacetyl acetone, palladium diacetonitrile dichloride or palladium dibenzonitrile dichloride; and/or, the said phosphine ligand is one or more of triphenylphosphine, tris (2-furanyl) phosphine, tris (4-methoxyphenyl) phosphine, tris (2,4,6-trimethoxyphenyl) phosphine, 1,1'-binaphthalene-2,2'-bisdiphenylphosphine, tricyclohexylphosphine, tri-n-butylphosphine or tri-tert-butylphosphine; and/or, the said palladium and phosphine complexes are one or more of tetratriphenylphosphine palladium, ditriphenylphosphine palladium dichloride, ditricyclohexylphosphine palladium or ditritert-butylphosphine palladium; and/or, the said solvents are one or more of water, benzene, toluene, p-xylene, o-xylene, m-xylene, mesitylene, 1,4-dioxane, tetrahydrofuran, ethylene glycol dimethyl ether, N,N-dimethylformamide, dimethyl sulfoxide; and/or, the said reaction temperature is 20-200° C.

5. The method of claim 3, wherein, in step (2), the molar ratio of the said biaryl compound:chiral amine:base:palladium salt:phosphine ligand is 1:(1~2):(1~2):(0.01~0.2):(0.01~0.2); and/or, the molar ratio of the said biaryl compound:chiral amine:base:palladium and phosphine complex is 1:(1~2):(1~2):(0.01~0.2); and/or, the said base is one or more of sodium bicarbonate, sodium carbonate, sodium hydroxide, potassium bicarbonate, potassium carbonate, potassium hydroxide, potassium phosphate or cesium carbonate; and/or, the said palladium salts are one or more of palladium acetate, palladium chloride, palladium dibenzylidenyl acetone, cinnamyl palladium chloride, allyl palladium chloride, palladium trifluoroacetate, palladium diacetyl acetone, palladium diacetonitrile dichloride or palladium dibenzonitrile dichloride; and/or, the said phosphine ligand is one or more of triphenylphosphine, tris (2-furanyl) phosphine, tris (4-methoxyphenyl) phosphine, tris (2,4,6-trimethoxyphenyl) phosphine, 1,1'-binaphthalene-2,2'-bisdiphenylphosphine, tricyclohexylphosphine, tri-n-butylphosphine or tri-tert-butylphosphine; and/or, the said palladium and phosphine complexes are one or more of tetratriphenylphosphine palladium, ditriphenylphosphine palladium dichloride, ditricyclohexylphosphine palladium or ditritert-butylphosphine palladium; and/or, the said solvent is one or more of benzene, toluene, p-xylene, o-xylene, m-xylene, mesitylene, tetrahydrofuran, 1,4-dioxane or ethylene glycol dimethyl ether, N,N-dimethylformamide or dimethyl sulfoxide; and/or, the said reaction temperature is 20-200° C.

6. The method of claim 3, wherein, in step (3), the molar ratio of the said amination product:acid is 1:(1~100); and/or, the said solvent is one or more of methanol, ethanol, isopropyl alcohol, water, 1,4-dioxane, tetrahydrofuran, ethylene glycol dimethyl ether, N,N-dimethylformamide or dimethyl sulfoxide; and/or, the said acid is one or more of hydrochloric acid, hydrobromic acid, hydroiodic acid, acetic acid, sulfuric acid, phosphoric acid, trifluoroacetic acid or p-toluenesulfonic acid; and/or, the said reaction temperature is −20-100° C.

7. The method of claim 3, wherein, in step (4), the molar ratio of the said phenolic products:trifluoromethosulfonation reagent:acid binding agent:4-dimethylaminopyridine is 1:(1~2):(1~2):(0.01~0.2); and/or, the said organic solvent is one or more of dichloromethane, 1,2-dichloroethane, N,N-dimethylformamide, tetrahydrofuran, ethylene glycol dimethyl ether or dimethyl sulfoxide; and/or, the said acid binding agent is an organic base, selected from one or more of 1,4-diazacycle [2.2.2]octane, N,N-diisopropyl ethylamine, triethylamine or pyridine; and/or, the said trifluorometalesulfonation reagent is one or more of trifluorometalesulfonyl anhydride, n-phenylbis (trifluorometalesulfonyl) imide or trifluorometalesulfonyl chloride; and/or, the said reaction temperature is −20-100° C.

8. The method of claim 3, wherein, in step (5), the molar ratio of the said trifluorometalesulfonation product:diphenyl phosphine:nickel:organic base is 1:(1~4): (0.05~0.2):(1~5); and/or, the said organic solvent is one or more of N,N-dimethylformamide, N-methylpyrrolidone or dimethyl sulfoxide; and/or, the said nickel is one or more of 1,2-bis (diphenylphosphine) ethane nickel chloride, 1,2-bis(diphenylphosphine) propane nickel chloride, 1,2-bis(diphenylphosphine) butane nickel chloride or ditriphenylphosphine nickel chloride; and/or, the said organic base is one or more of 1,4-diazacycle[2.2.2]octane, N,N-diisopropyl ethylamine, triethylamine or pyridine; and/or, the said reaction temperature is 70-140° C.
9. A class of phosphine nitrogen ligand intermediate with multiple chiral centers, wherein, the structures are as formula 3, 4, 5 and 6:
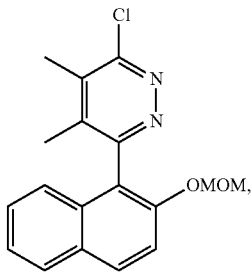
3
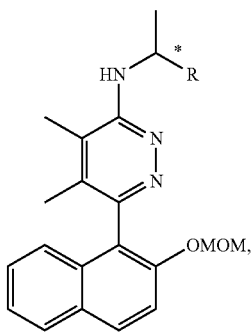
4
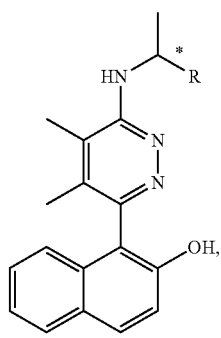
5
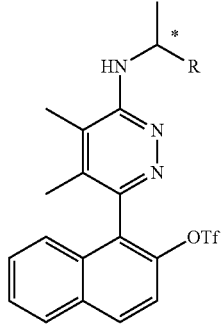
6
wherein,
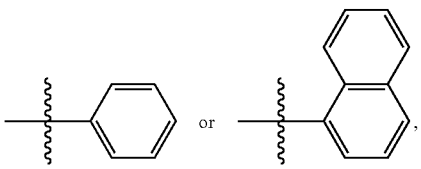
*represents the chiral center.